(12) United States Patent
Blumberg et al.

(10) Patent No.: US 7,417,041 B2
(45) Date of Patent: Aug. 26, 2008

(54) IMIDAZOPYRIMIDINES AS TRANSFORMING GROWTH FACTOR (TGF) INHIBITORS

(75) Inventors: Laura C. Blumberg, Waterford, CT (US); Michael J. Munchhof, Salem, CT (US); Andrei Shavnya, East Lyme, CT (US)

(73) Assignees: Pfizer Inc., New York, NY (US); Pfizer Products Inc., Groton, CT (US)

( * ) Notice: Subject to any disclaimer, the term of this patent is extended or adjusted under 35 U.S.C. 154(b) by 553 days.

(21) Appl. No.: 10/783,251

(22) Filed: Feb. 20, 2004

(65) Prior Publication Data

US 2004/0176390 A1    Sep. 9, 2004

Related U.S. Application Data

(60) Provisional application No. 60/451,683, filed on Mar. 4, 2003.

(51) Int. Cl.
| | |
|---|---|
| A61K 31/538 | (2006.01) |
| A61K 31/519 | (2006.01) |
| A61K 31/517 | (2006.01) |
| A61K 31/5025 | (2006.01) |
| A61K 31/502 | (2006.01) |
| A61K 31/4439 | (2006.01) |
| A61K 31/437 | (2006.01) |
| A61K 31/4375 | (2006.01) |
| A61K 31/4704 | (2006.01) |
| C07D 265/36 | (2006.01) |
| C07D 487/04 | (2006.01) |
| C07D 401/14 | (2006.01) |
| C07D 241/40 | (2006.01) |
| C07D 471/04 | (2006.01) |
| C07D 221/04 | (2006.01) |
| C07D 215/12 | (2006.01) |
| C07D 213/26 | (2006.01) |

(52) U.S. Cl. ............. 514/230.5; 544/105; 544/263; 544/281; 544/284; 544/235; 544/353; 544/333; 546/117; 546/119; 546/120; 546/121; 546/122; 546/112; 546/250; 514/259.31; 514/266.2; 514/248; 514/249; 514/256; 514/300; 514/303; 514/299; 514/332; 514/341

(58) Field of Classification Search ............ 544/105, 544/263, 281, 284, 235, 353, 333; 546/117, 546/119, 120, 121, 122, 114, 350; 514/230.5, 514/259.31, 266.2, 248, 249, 256, 300, 303, 514/299, 332, 341

See application file for complete search history.

(56) References Cited

U.S. PATENT DOCUMENTS

| | | | |
|---|---|---|---|
| 3,119,742 A | 1/1964 | Heimlich et al. | ............... 167/82 |
| 3,492,397 A | 1/1970 | Peters et al. | ............... 424/20 |
| 3,538,214 A | 11/1970 | Polli et al. | ............... 424/19 |
| 4,060,598 A | 11/1977 | Groppenbächer et al. | ............... 424/33 |
| 4,173,626 A | 11/1979 | Demski et al. | ............... 424/19 |
| 5,656,644 A | 8/1997 | Adams et al. | ............... 514/341 |
| 6,664,395 B2 | 12/2003 | Letavic et al. | ............... 544/405 |
| 6,696,464 B2 | 2/2004 | McClure et al. | ............... 514/303 |
| 2003/0092749 A1 | 5/2003 | Dombroski et al. | |
| 2004/0106608 A1 | 6/2004 | Munchhof et al. | |
| 2004/0110797 A1 | 6/2004 | Munchhof et al. | |
| 2004/0110798 A1 | 6/2004 | Munchhof et al. | |
| 2004/0116473 A1 | 6/2004 | Munchhof et al. | |
| 2004/0116474 A1 | 6/2004 | Munchhof et al. | |

FOREIGN PATENT DOCUMENTS

| | | |
|---|---|---|
| EP | 0231622 | 8/1987 |
| EP | 0257897 | 3/1988 |
| EP | 0306300 | 3/1989 |
| EP | 0364204 | 4/1990 |
| WO | WO9630347 | 10/1996 |
| WO | WO9852937 | 11/1998 |
| WO | WO9852941 | 11/1998 |
| WO | WO0031063 | 6/2000 |
| WO | WO0061576 | 10/2000 |
| WO | WO0162756 | 8/2001 |
| WO | WO0172737 | 10/2001 |
| WO | WO0216359 | 2/2002 |
| WO | WO0240468 | 5/2002 |
| WO | WO0240476 | 5/2002 |
| WO | WO02055077 | 7/2002 |
| WO | WO02062787 | 8/2002 |

(Continued)

OTHER PUBLICATIONS

Strutz (Expert Opin. Investig. Drugs, 2001, 10(11), 1989-2001).*

(Continued)

Primary Examiner—Brenda Coleman
Assistant Examiner—Susanna Moore
(74) Attorney, Agent, or Firm—Christine S. Lee; John H. Engelmann

(57) ABSTRACT

Novel fused heteroaromatic compounds, including derivatives thereof, to intermediates for their preparation, to pharmaceutical compositions containing them and to their medicinal use are described. The compounds of the present invention are potent inhibitors of transforming growth factor ("TGF")-β signaling pathway. They are useful in the treatment of various TGF-related disease states including, for example, cancer and fibrotic diseases.

6 Claims, No Drawings

FOREIGN PATENT DOCUMENTS

| WO | WO02062794 | 8/2002 |
| WO | WO02066462 | 8/2002 |
| WO | WO02072576 | 9/2002 |
| WO | WO0300682 | 1/2003 |
| WO | WO03087304 | 10/2003 |
| WO | WO2004013135 | 2/2004 |
| WO | WO2004013138 | 2/2004 |
| WO | WO2004021989 | 3/2004 |

OTHER PUBLICATIONS

Klose, W., et al., "Synthese von Pyridylphenyl-imidazo[2,1-b]thiazolen", *J. Heterocyclic Chem.*, vol. 22, pp. 669-671 (1985).

Callahan J., et al., Indentification of Novel Inhibitors of the Transforming Growth Factor β1 (TGF-β1) Type 1 Receptor (ALK5), *J. Med. Chem.*, vol. 45, pp. 999-1001 (2002). Published on Web Jan. 30, 2002.

Database Chemabs Online, Chemical Abstracts Service, CAPLUS Database Accession No. 1989:94933.

Laping, et al., "Inhibition of Transforming Growth Factor (TGF)-β1-Induced Extracellular Matrix with a Novel Inhibitor of the TGF-βType I Receptor Kinase Activity: SB-431542", Mol. Pharmacol., 62:58-64, 2002.

Moran, et al., "Synthesis of (Pyridinyl)-1,2,4-triazolo[4,3-α]pyridines" J. Heterocycl. Chem., 23:1071-1077, 1986.

Singh, et al., "Successful Shap-Based Virtual Screening: The Discovery of a Potent Inhibitor of the Type I TGFβ Receptor Kinase (TβRI)", Bioorganic & Medicinal Chemistry Letters, 13, pp. 4355-4359 (2003).

* cited by examiner

IMIDAZOPYRIMIDINES AS TRANSFORMING GROWTH FACTOR (TGF) INHIBITORS

RELATED APPLICATIONS

This application claims benefit of priority under 35 U.S.C. § 119(e) to U.S. Provisional Application No. 60/451,683, filed Mar. 4, 2003, which is incorporated herein in its entirety by reference.

BACKGROUND OF THE INVENTION

The present invention relates to novel fused heteroaromatic compounds, including derivatives thereof, to intermediates for their preparation, to pharmaceutical compositions containing them and to their medicinal use. The compounds of the present invention are potent inhibitors of the transforming growth factor ("TGF")-β signaling pathway. They are useful in the treatment of TGF-β related disease states including, for example, cancer and fibrotic diseases.

TGF-β activates both antiproliferative and tumor-promoting signaling cascades. Three mammalian TGF-β isoforms have been identified (TGF-βI, -βII, and -βIII). TGF-β production promotes tumor progression while its blockade enhances antitumor activity. Blockade of TGF-β enhances antitumor immune responses and inhibits metastasis. Thus there exists a need in the art for compounds that inhibit the TGF-β signaling pathway. The present invention, as described below, answers such a need.

SUMMARY OF THE INVENTION

The present invention provides a novel compound containing a core fused heteroaromatic substituted with at least one substituted or unsubstituted 2-pyridyl moiety and at least one $R^1$ moiety as set forth herein, and all pharmaceutically acceptable salts, prodrugs, tautomers, hydrates, and solvates thereof.

The present invention provides a compound of the formula (Ia) or (Ib):

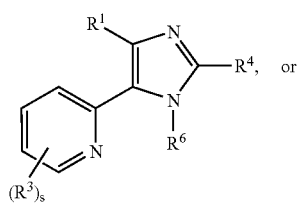
(Ia)

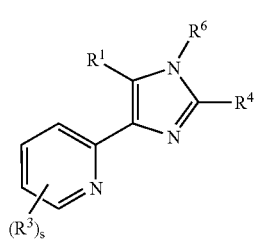
(Ib)

and all pharmaceutically acceptable salts, tautomers, prodrugs, hydrates, and solvates thereof, where

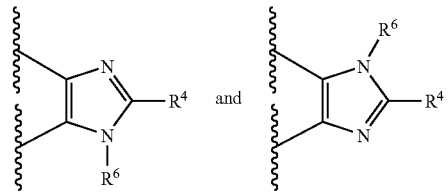

moieties of formulae (Ia) and (Ib) respectively, represent a core fused heteroaromatic. As would be understood by one of skill in the art, a core fused heteroaromatic, including all pharmaceutically acceptable salts, tautomers, prodrugs, hydrates, and solvates, each as described herein, can be further substituted, as defined below.

In formulae (Ia) and (Ib) above:

$R^1$ is a saturated, unsaturated, or aromatic $C_3$-$C_{20}$ mono-, bi- or polycyclic ring optionally containing at least one heteroatom selected from the group consisting of N, O and S, wherein $R^1$ can optionally be further independently substituted with at least one moiety independently selected from the group consisting of, but not limited to, hydrogen, carbonyl, halo, halo($C_1$-$C_6$)alkyl, perhalo($C_1$-$C_6$)alkyl, perhalo($C_1$-$C_6$)alkoxy, ($C_1$-$C_6$)alkyl, ($C_2$-$C_6$)alkenyl, ($C_2$-$C_6$)alkynyl, hydroxy, oxo, mercapto, ($C_1$-$C_6$)alkylthio, ($C_1$-$C_6$)alkoxy, ($C_5$-$C_{10}$)aryl or ($C_5$-$C_{10}$)heteroaryl, ($C_5$-$C_{10}$)aryloxy or ($C_5$-$C_{10}$)heteroaryloxy, ($C_5$-$C_{10}$)ar($C_1$-$C_6$)alkyl or ($C_5$-$C_{10}$)heteroar($C_1$-$C_6$)alkyl, ($C_5$-$C_{10}$)ar($C_1$-$C_6$)alkoxy or ($C_5$-$C_{10}$)heteroar($C_1$-$C_6$)alkoxy, HO—(C=O)—, keto, formyl, ester, amido, ether, amino, hydroxyamino, carboxy, guanidine, ureido, carbamoyl, phenyl($C_1$-$C_6$)alkyl, phenyl-O—($C_1$-$C_6$) alkyl, phenyl-S—($C_1$-$C_6$)alkyl, phenyl-NH—($C_1$-$C_6$)alkyl, aminocarbonyl, ($C_1$-$C_6$)alkyl- and di($C_1$-$C_6$)alkylamino, cyano, nitro, carbamoyl, ($C_1$-$C_6$)alkylcarbonyl, ($C_1$-$C_6$) alkoxycarbonyl, ($C_1$-$C_6$)alkylaminocarbonyl, di($C_1$-$C_6$)alkylaminocarbonyl, ($C_5$-$C_{10}$)arylcarbonyl, ($C_5$-$C_{10}$)aryloxycarbonyl, ($C_1$-$C_6$)alkylsulfonyl, and ($C_5$-$C_{10}$)arylsulfonyl;

more preferably, the $R^1$ substituent is independently selected from hydrogen, halo, hydroxy, amino, hydroxyamino, carboxy, ($C_1$-$C_6$)alkoxycarbonyl, nitro, guanidine, ureido, carbamoyl, cyano, trifluoromethyl, $(R^8)_2$N-carbonyl, and phenyl-W—($C_1$-$C_6$)alkyl wherein W is selected from a single bond, O, S and NH; or each $R^1$ substituent is independently selected from cyano-($C_1$-$C_6$)alkyl and $R^9$ wherein $R^9$ is selected from the group consisting of $R^5$, $R^5$O, $(R^5)_2$N, $R^7$C(=O), $R^5$ONH, A and $R^5$Y; $R^5$ is ($C_1$-$C_6$) alkyl; $R^8$ is hydrogen or $R^5$ wherein the $R^5$s are the same or different; $R^7$ is $R^5$, $R^5$O or $(R^8)_2$N; A is selected from piperidino, morpholino, pyrrolidino and 4-$R^8$-piperazin-1-yl, imidazol-1-yl, 4-pyridon-1-yl, carboxy-($C_1$-$C_6$)alkyl; and Y is selected from S, SO, $SO_2$; the alkyl moieties in $R^5$, $R^5$O and $(R^8)_2$N are optionally substituted with halo or $R^9$ wherein $R^9$ is defined as above, and wherein the resulting groups are optionally substituted with halo or $R^9$;

or each $R^1$ substituent is independently selected from $R^5$-sulfonlyamino, phthalimido-($C_1$-$C_6$)alkylsulfonylamino, benzamido, benzenesulfonylamino, 3-phenylureido, 2-oxopyrrolidin-1-yl, 2,5-dioxopyrrolidin-1-yl, and $R^{10}$—($C_1$-$C_6$)-alkanoylamino wherein $R^{10}$ is selected from halo, $R^8$O, ($C_1$-$C_6$)-alkanoyloxy, $R^7$C(=O), and $(R^8)_2$N; and wherein said benzamido or benzenesulfonylamino or phenyl or phenoxy or anilino or phenylsulfanyl substituent in $R^1$ may optionally bear one or two halogens, ($C_1$-$C_6$)alkyl, cyano, methanesulfonyl or ($C_1$-$C_6$)alkoxy substituents, wherein $R^5$, $R^7$ and $R^8$ are each as defined above;

or any two adjacent R¹ substituents take, together with the carbons to which they are attached comprise a 5-8 membered ring comprising at least one or two heteroatoms selected from oxygen, sulfur or nitrogen; and wherein the alkyl groups and alkyl portions of the alkoxy or alkylamino groups may be straight chained or if comprised of at least three carbons may be branched or cyclic;

each R³ is independently selected from the group consisting of: hydrogen, halo, halo($C_1$-$C_6$)alkyl, ($C_1$-$C_6$)alkyl, ($C_2$-$C_6$)alkenyl, ($C_2$-$C_6$)alkynyl, perhalo($C_1$-$C_6$)alkyl, ($C_5$-$C_{10}$)heteroaryl, ($C_5$-$C_{10}$)heterocyclic, ($C_3$-$C_{10}$)cycloalkyl, hydroxy, ($C_1$-$C_6$)alkoxy, perhalo($C_1$-$C_6$)alkoxy, phenoxy, ($C_5$-$C_{10}$)heteroaryl-O—, ($C_5$-$C_{10}$)heterocyclic-O—, ($C_3$-$C_{10}$)cycloalkyl-O—, ($C_1$-$C_6$)alkyl-S—, ($C_1$-$C_6$)alkyl-SO$_2$—, ($C_1$-$C_6$)alkyl-NH—SO$_2$—, nitro, cyano, amino, Ph(CH$_2$)$_{1-6}$NH—, ($C_1$-$C_6$)alkylamino, [($C_1$-$C_6$)alkyl]$_2$-amino, ($C_1$-$C_6$)alkyl-SO$_2$—NH—, amino(C=O)—, amino-SO$_2$—, ($C_1$-$C_6$)alkyl-(C=O)—NH—, ($C_1$-$C_6$)alkyl-(C=O)—[(($C_1$-$C_6$)alkyl)-N]—, phenyl-(C=O)—NH—, phenyl-(C=O)—[(($C_1$-$C_6$)alkyl)-N]—, ($C_1$-$C_6$)alkyl-(C=O)—, phenyl-(C=O)—, ($C_5$-$C_{10}$)heteroaryl-(C=O)—, ($C_5$-$C_{10}$)heterocyclic-(C=O)—, ($C_3$-$C_{10}$)cycloalkyl-(C=O)—, HO—(C=O)—, ($C_1$-$C_6$)alkyl-O—(C=O)—, H$_2$N(C=O)—($C_1$-$C_6$)alkyl-NH—(C=O)—, [($C_1$-$C_6$)alkyl]$_2$—N—(C=O)—, phenyl-NH—(C=O)—, phenyl-[(($C_1$-$C_6$)alkyl)-N]—(C=O)—, ($C_5$-$C_{10}$)heteroaryl-NH—(C=O)—, ($C_5$-$C_{10}$)heterocyclic-NH—(C=O)—, ($C_3$-$C_{10}$)cycloalkyl-NH—(C=O)— and ($C_1$-$C_6$)alkyl-(C=O)—O—, where R³ is optionally substituted by at least one substituent independently selected from ($C_1$-$C_6$)alkyl, ($C_1$-$C_6$)alkoxy, halo($C_1$-$C_6$)alkyl, halo, H$_2$N—, Ph(CH$_2$)$_{1-6}$NH—, and ($C_1$-$C_6$)alkylNH—;

preferably, R³ is a ($C_1$-$C_6$)alkyl or a ($C_3$-$C_{10}$)cycloalkyl group;

more preferably, R³ is a methyl or a cyclopropyl group;

s is an integer from one to five;

preferably, an integer from one to four; and

R⁴ and R⁶ taken together with the atoms to which they are attached form a core fused heteroaromatic, as defined below;

preferably, R⁴ and R⁶ are taken together with the atoms to which they are attached form a substituted or unsubstituted 5- to 6-membered heteroaromatic ring system containing one or more heteroatoms selected from N, O and S, where the substituents are as set forth below.

As would be understood by one of skill in the art, rotation about the single bonds of the compounds of formulae (Ia) and (Ib) may occur to give different regioisomers. Thus, formulae (Ia) and (Ib) include all possible regioisomers. In one embodiment of the invention, the regioisomer illustrated above as formula (Ib) is preferred.

In another embodiment of the invention, the core fused heteroaromatic is:

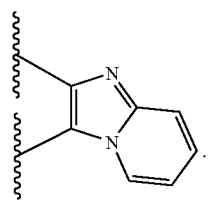

In another embodiment of the invention, the core fused heteroaromatic is:

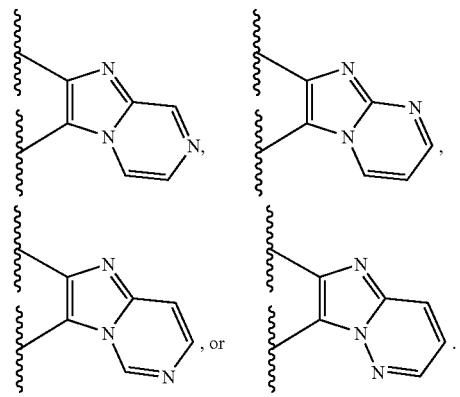

In another embodiment of the invention, the core fused heteroaromatic is:

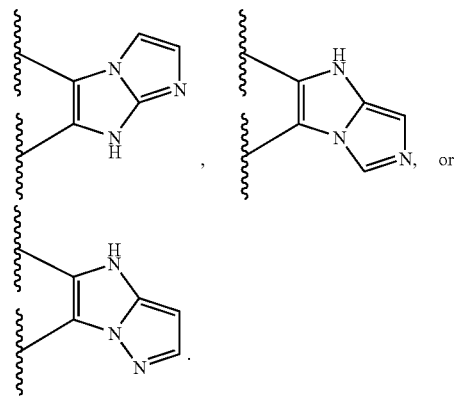

In another embodiment of the invention, the core fused heteroaromatic is:

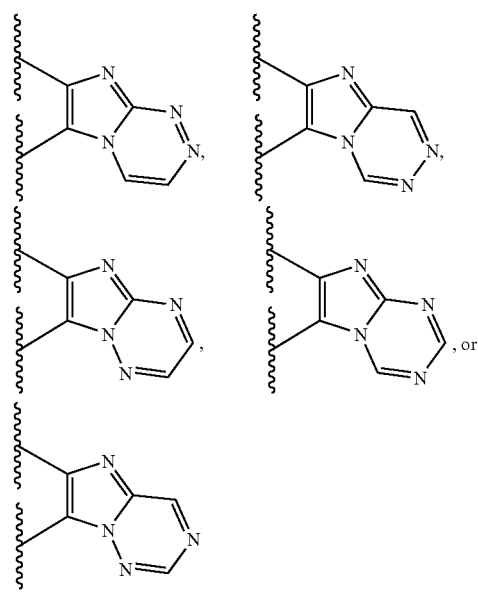

In another embodiment of the invention, the core fused heteroaromatic is:

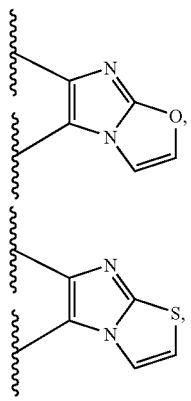 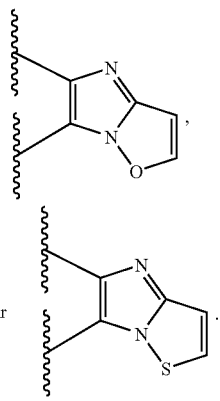

or

In another embodiment of the invention, the core fused heteroaromatic is:

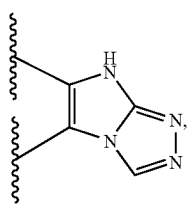 or 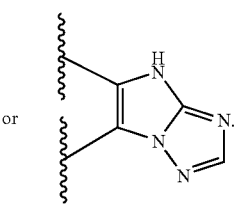

In another embodiment of the invention, the core fused heteroaromatic is:

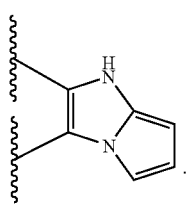

In another embodiment of the invention, the core fused heteroaromatic is:

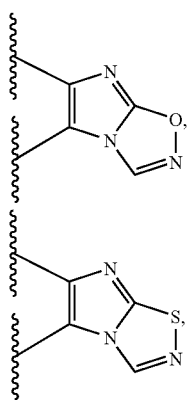 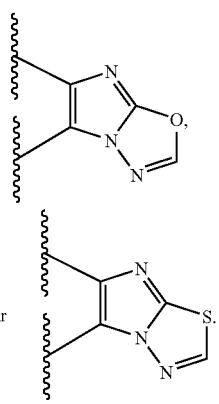

or 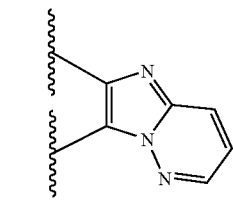

In another embodiment of the invention, the core fused heteroaromatic is:

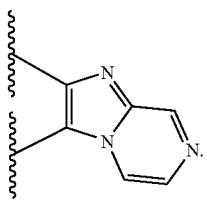

In another embodiment of the invention, the core fused heteroaromatic is:

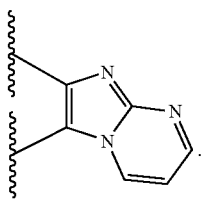

In another embodiment of the invention, the core fused heteroaromatic is:

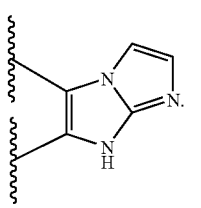

In another embodiment of the invention, the core fused heteroaromatic is:

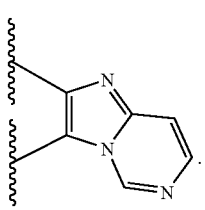

In another embodiment of the invention, the core fused heteroaromatic is:

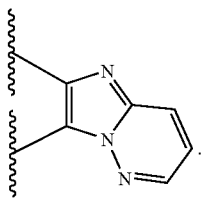

In another embodiment of the invention, the core fused heteroaromatic is:

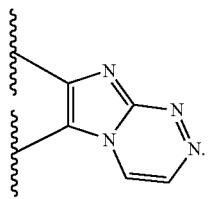

In another embodiment of the invention, the core fused heteroaromatic is:

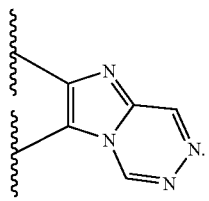

In another embodiment of the invention, the core fused heteroaromatic is:

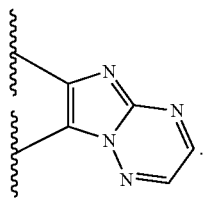

In another embodiment of the invention, the core fused heteroaromatic is:

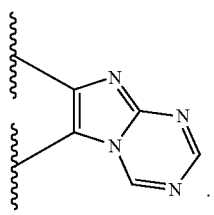

In another embodiment of the invention, the core fused heteroaromatic is:

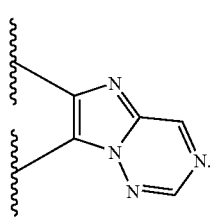

In another embodiment of the invention, the core fused heteroaromatic is:

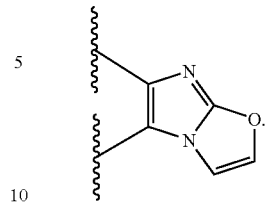

In another embodiment of the invention, the core fused heteroaromatic is:

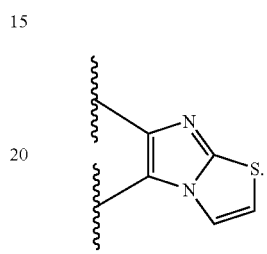

In another embodiment of the invention, the core fused heteroaromatic is:

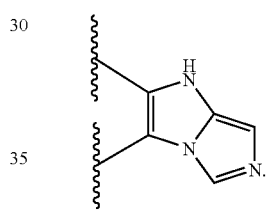

In another embodiment of the invention, the core fused heteroaromatic is:

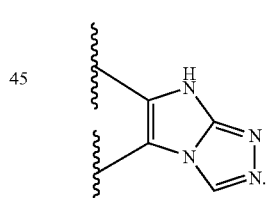

In another embodiment of the invention, the core fused heteroaromatic is:

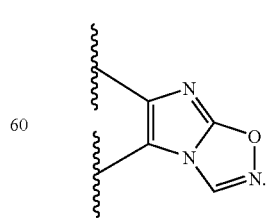

In another embodiment of the invention, the core fused heteroaromatic is:

In another embodiment of the invention, the core fused heteroaromatic is:

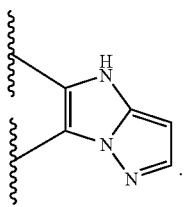

In another embodiment of the invention, the core fused heteroaromatic is:

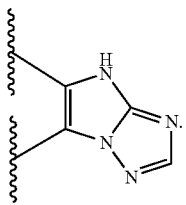

In another embodiment of the invention, the core fused heteroaromatic is:

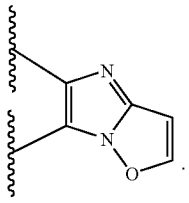

In another embodiment of the invention, the core fused heteroaromatic is:

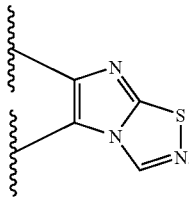

In another embodiment of the invention, the core fused heteroaromatic is:

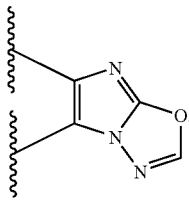

In another embodiment of the invention, the core fused heteroaromatic is:

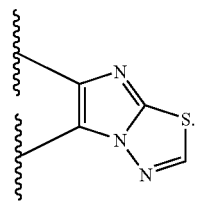

In another embodiment of the invention, the core fused heteroaromatic is:

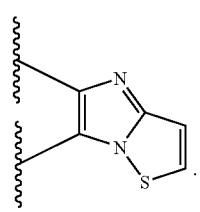

In another embodiment of the invention, $R^1$ of formulae (Ia)-(Ib), each as set forth above, is

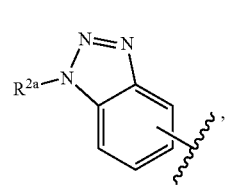 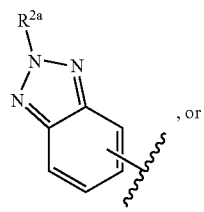

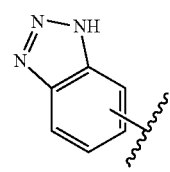

where $R^{2a}$ is as set forth herein.

In another embodiment of the invention, $R^1$ of formulae (Ia)-(Ib), each as set forth above, is

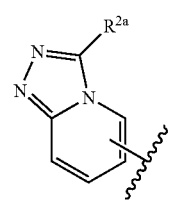 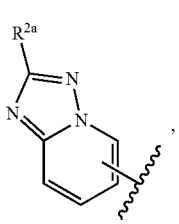

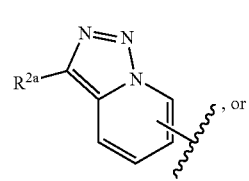 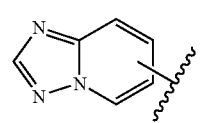

where $R^{2a}$ is as set forth herein.

In another embodiment of the invention, $R^1$ of formulae (Ia)-(Ib), each as set forth above, is

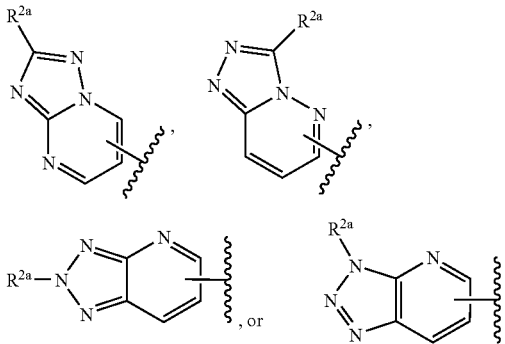

where $R^{2a}$ is as set forth herein.

In another embodiment of the invention, $R^1$ of formulae (Ia)-(Ib), each as set forth above, is

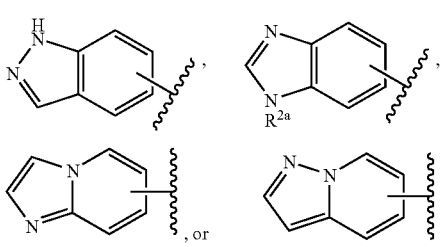

where $R^{2a}$ is as set forth herein.

In another embodiment of the invention, $R^1$ of formulae (Ia)-(Ib), each as set forth above, is

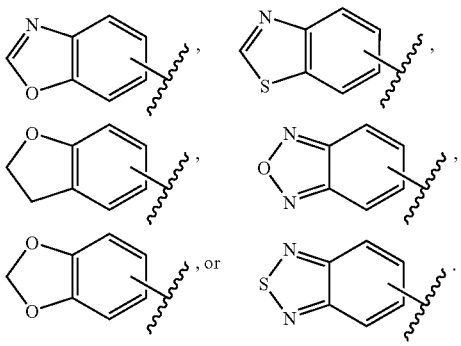

In another embodiment of the invention, $R^1$ of formulae (Ia)-(Ib), each as set forth above, is

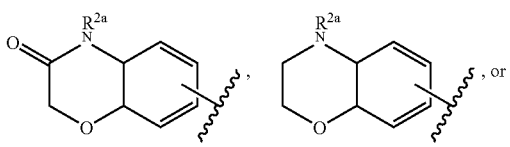

-continued

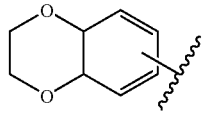

where $R^{2a}$ is as set forth herein.

In another embodiment of the invention, $R^1$ of formulae (Ia)-(Ib), each as set forth above, is

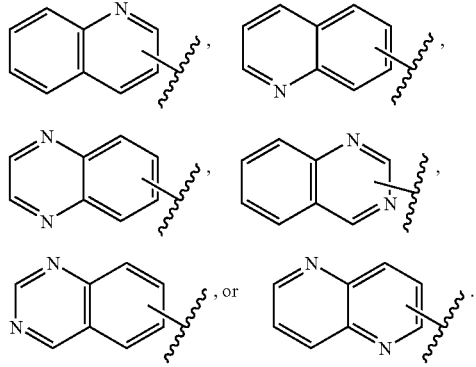

In another embodiment of the invention, $R^1$ of formulae (Ia)-(Ib), each as set forth above, is

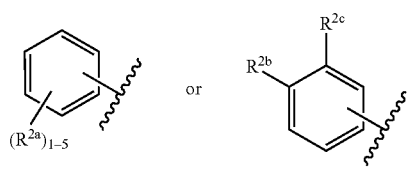

where $R^{2a}$, $R^{2b}$, and $R^{2c}$ are each as set forth herein.

In another embodiment of the invention, $R^1$ of formulae (Ia-(Ib), each as set forth above, is

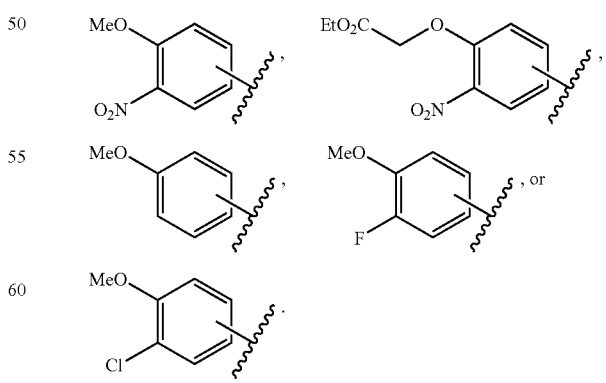

In another embodiment of the invention, $R^1$ of formulae (Ia)-(Ib), each as set forth above, is

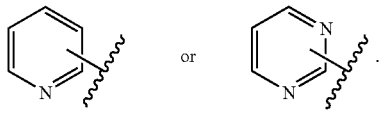

In another embodiment of the invention, $R^1$ of formulae (Ia)-(Ib), each as set forth above, is

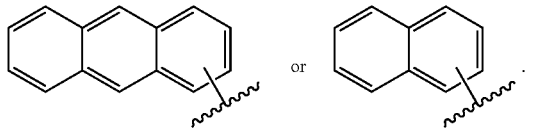

In another embodiment of the invention, $R^1$ of formulae (Ia)-(Ib), each as set forth above, is

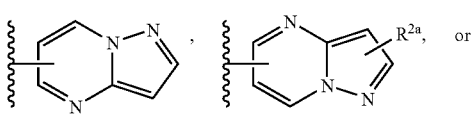

where $R^{2a}$ is as set forth herein.

In another embodiment of the invention, $R^1$ of formulae (Ia)-(Ib), each as set forth above, is

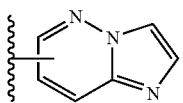

In another embodiment of the invention, $R^1$ of formulae (Ia)-(Ib), each as set forth above, is

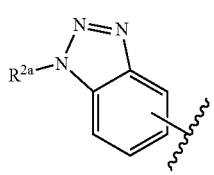

where $R^{2a}$ is as set forth herein.

In another embodiment of the invention, $R^1$ of formulae (Ia)-(Ib), each as set forth above, is

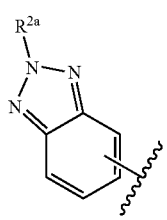

where $R^{2a}$ is as set forth herein

In another embodiment of the invention, $R^1$ of formulae (Ia)-(Ib), each as set forth above, is

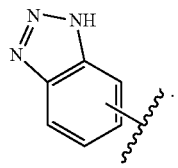

In another embodiment of the invention, $R^1$ of formulae (Ia)-(Ib), each as set forth above, is

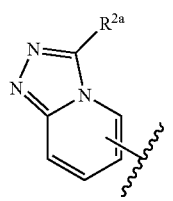

where $R^{2a}$ is as set forth herein.

In another embodiment of the invention, $R^1$ of formulae (Ia)-(Ib), each as set forth above, is

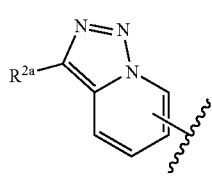

where $R^{2a}$ is as set forth herein

In another embodiment of the invention, $R^1$ of formulae (Ia)-(Ib), each as set forth above, is

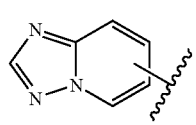

where $R^{2a}$ is as set forth herein

In another embodiment of the invention, $R^1$ of formulae (Ia)-(Ib), each as set forth above, is

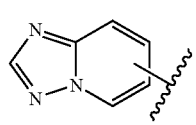

where $R^{2a}$ is as set forth herein.

In another embodiment of the invention, $R^1$ of formulae (Ia)-(Ib), each as set forth above, is

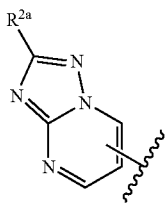

where $R^{2a}$ is as set forth herein.

In another embodiment of the invention, $R^1$ of formulae (Ia)-(Ib), each as set forth above, is

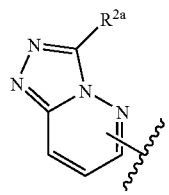

where $R^2$, is as set forth herein.

In another embodiment of the invention, $R^1$ of formulae (Ia)-(Ib), each as set forth above, is

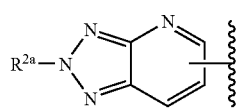

where $R^{2a}$ is as set forth herein.

In another embodiment of the invention, $R^1$ of formulae (Ia)-(Ib), each as set forth above, is

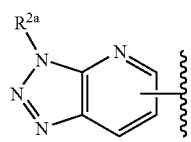

where $R^{2a}$ is as set forth herein.

In another embodiment of the invention, $R^1$ of formulae (Ia)-(Ib), each as set forth above, is

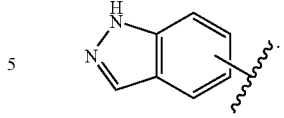

In another embodiment of the invention, $R^1$ of formulae (Ia)-(Ib), each as set forth above, is

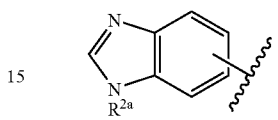

where $R^{2a}$ is as set forth herein.

In another embodiment of the invention, $R^1$ of formulae (Ia)-(Ib), each as set forth above, is

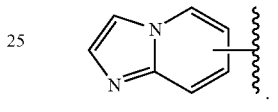

In another embodiment of the invention, $R^1$ of formulae (Ia)-(Ib), each as set forth above, is

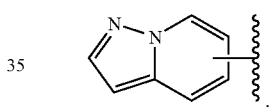

In another embodiment of the invention, $R^1$ of formulae (Ia)-(Ib), each as set forth above, is

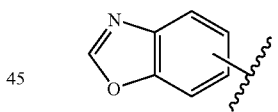

In another embodiment of the invention, $R^1$ of formulae (Ia)-(Ib), each as set forth above, is

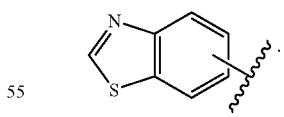

In another embodiment of the invention, $R^1$ of formulae (Ia)-(Ib), each as set forth above, is

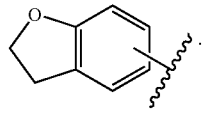

In another embodiment of the invention, $R^1$ of formulae (Ia)-(Ib), each as set forth above, is

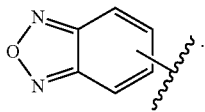

In another embodiment of the invention, $R^1$ of formulae (Ia)-(Ib), each as set forth above, is

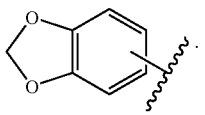

In another embodiment of the invention, $R^1$ of formulae (Ia)-(Ib), each as set forth above, is

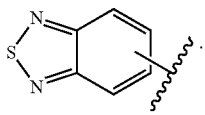

In another embodiment of the invention, $R^1$ of formulae (Ia)-(Ib), each as set forth above, is

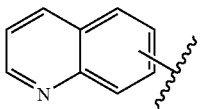

In another embodiment of the invention, $R^1$ of formulae (Ia)-(Ib), each as set forth above, is

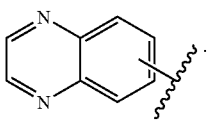

In another embodiment of the invention, $R^1$ of formulae (Ia)-(Ib), each as set forth above, is

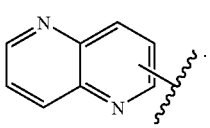

The invention also provides, a compound selected from the croup consisting of:
6-[2-(6-Methyl-pyridin-2-yl)-imidazo[1,2-a]pyridin-3-yl]-quinoline;
6-[2-(6-Methyl-pyridin-2-yl)-imidazo[1,2-a]pyrazin-3-yl]-quinoline;
6-[2-(6-Methyl-pyridin-2-yl)-imidazo[1,2-a]pyrimidin-3-yl]-quinoline;
2-Benzo[1,3]dioxol-5-yl-3-(6-methyl-pyridin-2-yl)-1H-imidazo[1,2-a]imidazole;
2-Benzo[1,3]dioxol-5-yl-3-(6-methyl-pyridin-2-yl)-imidazo[1,2-a]pyrimidine;
6-[2-(6-Methyl-pyridin-2-yl)-imidazo[1,2-a]pyrazin-3-yl]-quinoline;
6-[3-(6-Methyl-pyridin-2-yl)-imidazo[1,2-a]pyridin-2-yl]-quinoline;
6-[3-(6-Methyl-pyridin-2-yl)-imidazo[1,2-a]pyrimidin-2-yl]-quinoline;
6-[6-(6-Methyl-pyridin-2-yl)-imidazo[2,1-b][1,3,4]thiadiazol-5-yl]-quinoline;
6-[6-(6-Methyl-pyridin-2-yl)-imidazo[2,1-b]thiazol-5-yl]-quinoline;
6-[8-Methyl-2-(6-methyl-pyridin-2-yl)-imidazo[1,2-a]pyridin-3-yl]-quinoline;
6-[7-Methyl-2-(6-methyl-pyridin-2-yl)-imidazo[1,2-a]pyridin-3-yl]-quinoline;
6-[6-Methyl-2-(6-methyl-pyridin-2-yl)-imidazo[1,2-a]pyridin-3-yl]-quinoline;
6-[3-(6-Methyl-pyridin-2-yl)-7H-imidazo[1,2-a]imidazol-2-yl]-quinoline;
1-Methyl-6-[3-(6-methyl-pyridin-2-yl)-imidazo[1,2-a]pyrimidin-2-yl]-1H-benzotriazole;
1-Methyl-6-[2-(6-methyl-pyridin-2-yl)-imidazo[1,2-a]pyridin-3-yl]-1H-benzotriazole;
6-[3-Methyl-6-(6-methyl-pyridin-2-yl)-imidazo[2,1-b]thiazol-5-yl]-quinoline;
6-[2-Methyl-6-(6-methyl-pyridin-2-yl)-imidazo[2,1-b]thiazol-5-yl]-quinoline;
6-[7-Methyl-2-(6-methyl-pyridin-2-yl)-imidazo[1,2-a]pyrimidin-3-yl]-quinoline;
2-(6-Methyl-pyridin-2-yl)-3-quinolin-6-yl-imidazo[1,2-a]pyrimidin-7-ylamine;
6-[7-Methyl-2-(6-methyl-pyridin-2-yl)-6-nitro-imidazo[1,2-a]pyridin-3-yl]-quinoline;
1-Methyl-6-[2-(6-methyl-pyridin-2-yl)-imidazo[1,2-a]pyrimidin-3-yl]-1H-benzotriazole;
1-Methyl-6-[6-(6-methyl-pyridin-2-yl)-imidazo[2,1-b]thiazol-5-yl]-1H-benzotriazole;
1-Methyl-6-[6-(6-methyl-pyridin-2-yl)-imidazo[2,1-b][1,3,4]thiadiazol-5-yl]-1H-benzotriazole;
2-Methyl-5-[2-(6-methyl-pyridin-2-yl)-imidazo[1,2-a]pyrimidin-3-yl]-2H-benzotriazole;
3-(2-Methyl-2H-benzotriazol-5-yl)-2-(6-methyl-pyridin-2-yl)-imidazo[1,2-a]pyrimidin-7-ylamine;
2-Methyl-5-[6-(6-methyl-pyridin-2-yl)-imidazo[2,1-b]thiazol-5-yl]-2H-benzotriazole;
2-Methyl-5-[6-(6-methyl-pyridin-2-yl)-imidazo[2,1-b][1,3,4]thiadiazol-5-yl]-2H-benzotriazole;
2-(6-Methyl-pyridin-2-yl)-3-quinolin-6-yl-imidazo[1,2-a]pyrimidin-7-ol;
1-Methyl-6-[6-(6-methyl-pyridin-2-yl)-2-methylsulfanyl-imidazo[2,1-b][1,3,4]thiadiazol-5-yl]-1H-benzotriazole;
Dimethyl-[2-(6-methyl-pyridin-2-yl)-3-quinolin-6-yl-imidazo[1,2-a]pyrimidin-7-yl]-amine;
2-Methyl-5-[3-methyl-6-(6-methyl-pyridin-2-yl)-imidazo[2,1-b]thiazol-5-yl]-2H-benzotriazole;
2-Methyl-5-[2-methyl-6-(6-methyl-pyridin-2-yl)-imidazo[2,1-b]thiazol-5-yl]-2H-benzotriazole;
2-(6-Methyl-pyridin-2-yl)-3-pyridin4-yl-imidazo[1,2-a]pyridine;
2-(6-Methyl-pyridin-2-yl)-3-pyridin-4-yl-imidazo[1,2-a]pyrimidine;
2-(6-Methyl-pyridin-2-yl)-3-pyridin-4-yl-imidazo[1,2-a]pyrimidin-7-ylamine;

3-Benzothiazol-6-yl-2-(6-methyl-pyridin-2-yl)-imidazo[1,2-a]pyrimidin-7-ylamine;
1-Methyl-6-[6-(6-cyclopropyl-pyridin-2-yl)-imidazo[2,1-b][1,3,4]thiadiazol-5-yl]-1H-benzotriazole;
3-Methyl-5-[6-(6-methyl-pyridin-2-yl)-imidazo[2,1-b]thiazol-5-yl]-3H-[1,2,3]triazolo[4,5-b]pyridine;
3-Methyl-5-[6-(6-methyl-pyridin-2-yl)-imidazo[2,1-b] [1,3,4]thiadiazol-5-yl]-3H-[1,2,3]triazolo[4,5-b]pyridine;
2-Methyl-5-[6-(6-methyl-pyridin-2-yl)-imidazo[2,1-b]thiazol-5-yl]-2H-[1,2,3]triazolo[4,5-b]pyridine;
2-Methyl-5-[6-(6-methyl-pyridin-2-yl)-imidazo[2,1-b] [1,3,4]thiadiazol-5-yl]-2H-[1,2,3]triazolo[4,5-b]pyridine; and
2-Methyl-5-[2-(6-methyl-pyridin-2-yl)-7H-imidazo[1,2-a]imidazol-3-yl]-2H-benzotriazole.

The invention also provides a pharmaceutical composition containing at least one compound of the invention and a pharmaceutically acceptable carrier.

The invention further provides a method of preparation of a compound of the invention.

The invention still further provides a method of preventing or treating a TGF-related disease state in an animal or human comprising the step of administering a therapeutically effective amount of at least one compound of the invention to the animal or human suffering from the TGF-related disease state.

A compound of the invention can be used in the manufacture of a medicament for the prophylactic or therapeutic treatment of a TGF-related disease state in a mammal (animal or human).

Definitions

As used herein, the article "a" or "an" refers to both the singular and plural form of the object to which it refers.

As used herein; the term "alkyl," as well as the alkyl moieties of mother groups referred to herein (e.g., alkoxy) refers to a linear or branched saturated hydrocarbon (e.g., methyl, ethyl, n-propyl, isopropyl, n-butyl, iso-butyl, secondary-butyl, tertiary-butyl).

As used herein, the term "cycloalkyl" refers to a mono or bicyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl).

As used herein, the term "halogen" or "halo" refers to fluoro, chloro, bromo or iodo or fluoride, chloride, bromide or iodide.

As used herein, the term "halo-substituted alkyl" or "haloalkyl" refers to an alkyl radical, as set forth above, substituted with one or more halogens, as set forth above, including, but not limited to, chloromethyl, dichloromethyl, fluoromethyl, difluoromethyl, trifluoromethyl, and 2,2,2-trichloroethyl.

As used herein, the term "perhaloalkyl" refers to an alkyl radical, as set forth above, where each hydrogen of the alkyl group is replaced with a "halogen" or "halo" as set forth above.

As used herein, the term "alkenyl" refers to a linear or branched hydrocarbon chain radical containing at least two carbon atoms and at least one double bond. Examples include, but are not limited to, ethenyl, 1-propenyl, 2-propenyl (allyl), iso-propenyl, 2-methyl-1-propenyl, 1-butenyl, and 2-butenyl.

As used herein, the term "alkynyl" refers to a linear or branched hydrocarbon chain radical having at least one triple bond including, but not limited to, ethynyl, propynyl, and butynyl.

As used herein, the term "carbonyl" refers to a C=O moiety. For example, alkoxycarbonylamino (i.e. alkoxy (C=O)—NH—) refers to an alkyl carbamate group.

As used herein, the term "phenyl-[(alkyl)-N]—(C=O)—" "refers to a N,N'-disubstituted amide group of the formula

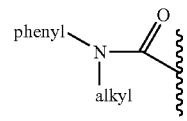

As used herein, the term "aryl" refers to an aromatic radical such as, for example, phenyl, naphthyl, tetrahydronaphthyl, and indanyl.

As used herein, the term "heteroaryl" or "heteroaromatic" refers to an aromatic or unsaturated group containing at least one heteroatom selected from O, S and N. For example, heteroaryl groups include, but are not limited to, pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, and indolyl.

As used herein, the term "heterocyclic" refers to a saturated or unsaturated $C_3$-$C_{20}$ mono-, bi- or polycyclic group containing at least one heteroatom selected from N, O, and S. Examples of heterocyclic groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxcithiazinyl, indolinyl, isoindolinyl, quincuclidinyl, chromanyl, isochromanyl, benzocazinyl, and the like. Examples of monocyclic saturated or unsaturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, and 1,2,5-oxathiazin-4-yl.

As used herein, the term "pharmaceutically acceptable acid addition salt" refers to non-toxic acid addition salts, i.e., salts derived from pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

As used herein, the term "pharmaceutically acceptable base addition salt" refers to non-toxic base addition salts, i.e., salts derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

As used herein, the term "suitable substituent", "substituent", or "substituted" refers to at least one chemically and pharmaceutically acceptable functional group, i.e., a moiety that does not negate the inhibitory and/or therapeutic activity of the inventive compounds and that can optionally be further substituted. Such suitable optionally substituted substituents may be routinely selected by those skilled in the art. Illustrative examples of suitable substituents include, but are not limited to, carbonyl, halo, haloalkyl, perfluoroalkyl, perfluoroalkoxy, alkyl, alkenyl, alkynyl, hydroxy, oxo, mercapto, alkylthio, alkoxy, aryl or heteroaryl, aryloxy or heteroaryloxy, aralkyl or heteroaralkyl, aralkoxy or heteroaralkoxy, HO—(C═O)—, ester, amido, ether, amino, alkyl- and dialkylamino, cyano, nitro, carbamoyl, alkylcarbonyl, alkoxycarbonyl, alkylaminocarbonyl, dialkylaminocarbonyl, arylcarbonyl, aryloxycarbonyl, alkylsulfonyl, arylsulfonyl and the like. These same substituents can be used for further substitution of any given substituent.

As used herein, the term "TGF-related disease state" refers to any disease state mediated by the production of TGF-β.

As used herein, the term "Ph" refers to phenyl.

As used herein, the term "a saturated, unsaturated, or aromatic $C_3$-$C_{20}$ mono-, bi- or polycyclic ring optionally containing at least one heteroatom" refers to, but is not limited to,

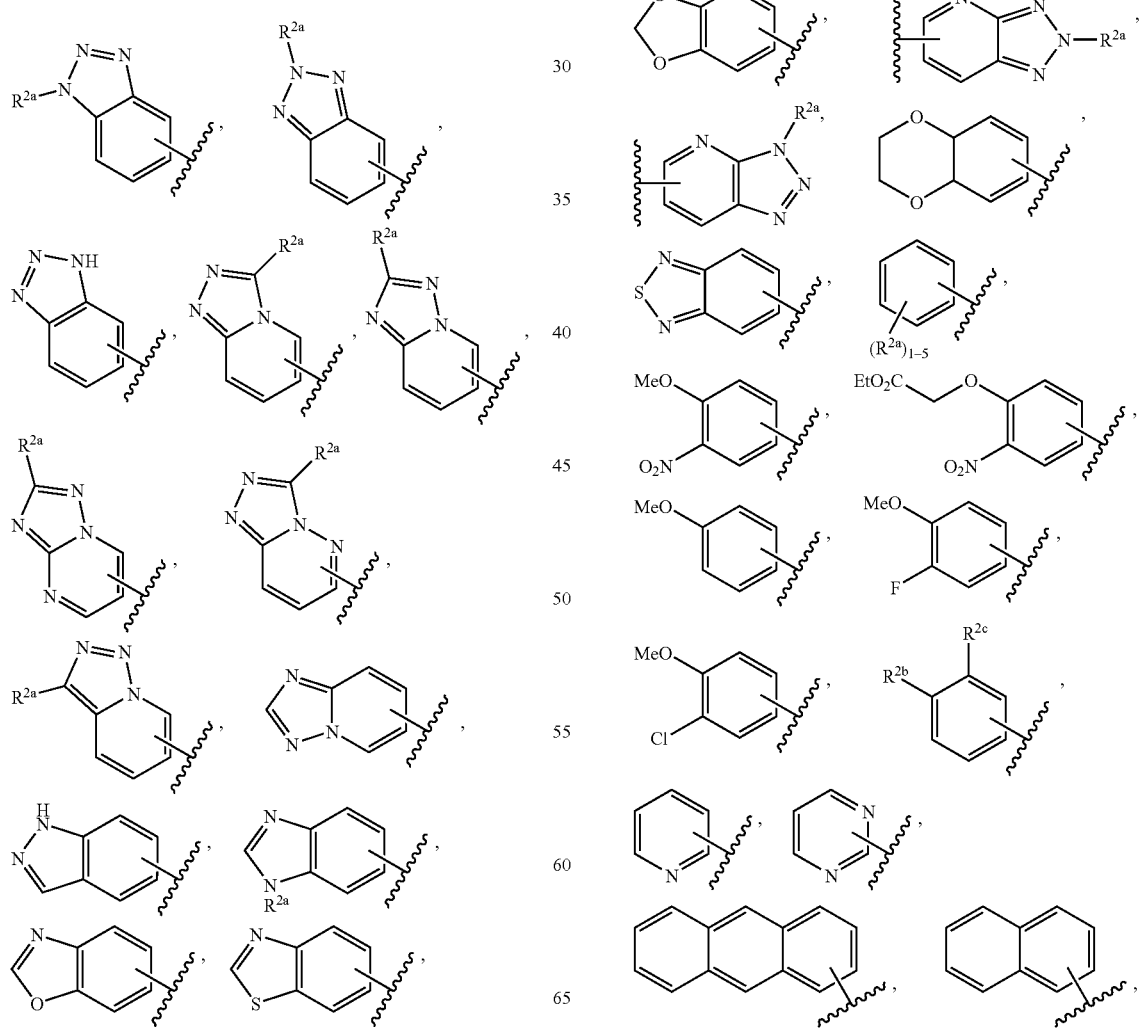

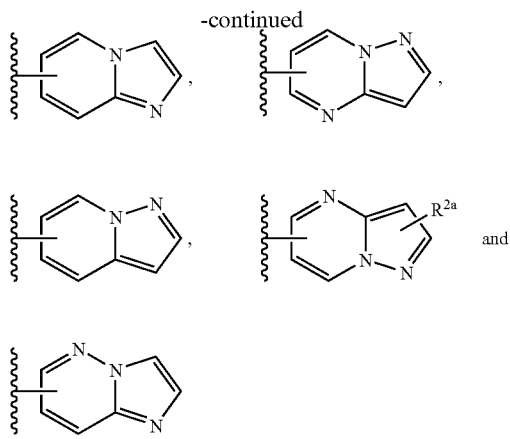

where $R^{2a}$ is independently selected from the group consisting of: hydrogen, $(C_1-C_6)$alkyl, $(C_2-C_6)$alkenyl, $(C_2-C_6)$alkynyl, $(C_3-C_{10})$cycloalkyl, $(C_5-C_{10})$aryl, $(C_1-C_6)$alky$(C_5-C_{10})$aryl, amino, carbonyl, $(C_1-C_6)$ester, $(C_5-C_{10})$heteroaryl, $(C_5-C_{10})$heterocyclyl, $(C_1-C_6)$alkoxy, nitro, halo, hydroxyl, $(C_1-C_6)$alkoxy$(C_1-C_6)$ester, and those groups described in U.S. application Ser. Nos. 10/094,717, 10/094,760, and 10/115,952, each of which is herein incorporated in its entirety by reference; and where alkyl, alkenyl, alkynyl, cycloalkyl, aryl, amino, acid, ester, heteroaryl, heterocyclyl, and alkoxy of $R^{2a}$ is optionally substituted by at least one moiety independently selected from the group consisting of hydrogen, halo, $(C_1-C_6)$alkyl, $(C_2-C_6)$alkenyl, $(C_2-C_6)$alkynyl, perhalo$(C_1-C_6)$alkyl, phenyl, $(C_3-C_{10})$cycloalkyl, $(C_5-C_{10})$heteroaryl, $(C_5-C_{10})$heterocyclic, formyl, —CN, $(C_1-C_6)$alkyl-(C=O)—, phenyl-(C=O)—, HO—(C=O)—, $(C_1-C_6)$alkyl-O—(C=O)—, $(C_1-C_6)$alkyl-NH—(C=O)—, $((C_1-C_6)$alkyl$)_2$—N—(C=O)—, phenyl-NH—(C=O)—, phenyl-[$((C_1-C_6)$alkyl)-N]—(C=O)—, nitro, amino, $(C_1-C_6)$alkylamino, $((C_1-C_6)$alkyl$)_2$-amino, $(C_1-C_6)$alkyl-(C=O)—NH—, $(C_1-C_6)$alkyl-(C=O)—[$((C_1-C_6)$alkyl)-N]—, phenyl-(C=O)—NH—, phenyl-(C=O)—[$((C_1-C_6)$alkyl)-N]—, $H_2N$—(C=O)—NH—, $(C_1-C_6)$alkyl-HN—(C=O)—NH—, $((C_1-C_6)$alkyl$)_2$N—(C=O)—NH—, $(C_1-C_6)$alkyl-HN—(C=O)-[$((C_1-C_6)$alkyl)-N]-, $((C_1-C_6)$alkyl$)_2$N—(C=O)—[$(C_1-C_6)$alkyl-N]—, phenyl-HN—(C=O)—NH—, (phenyl$)_2$N—(C=O)—NH—, phenyl-HN—(C=O)—[$((C_1-C_6)$alkyl)-N]—, (phenyl-$)_2$N—(C=O)—[$((C_1-C_6)$alkyl)-N]—, $(C_1-C_6)$alkyl-O—(C=O)—NH—, $(C_1-C_6)$alkyl-O—(C=O)—[$((C_1-C_6)$alkyl)-N]—, phenyl-O—(C=O)—NH—, phenyl-O—(C=O)—[$((C_1-C_6)$alkyl)-N]—, $(C_1-C_6)$alkyl-$SO_2$NH—, phenyl-$SO_2$NH—, $(C_1-C_6)$alkyl-$SO_2$—, phenyl-$SO_2$—, hydroxy, $(C_1-C_6)$alkoxy, perhalo$(C_1-C_6)$alkoxy, phenoxy, $(C_1-C_6)$alkyl-(C=O)—O—, $(C_1-C_6)$ester-$(C_1-C_6)$alkyl-O—, phenyl-(C=O)—O—, $H_2N$—(C=O)—O—, $(C_1-C_6)$alkyl-HN—(C=O)—O—, $((C_1-C_6)$alkyl$)_2$N—(C=O)—O—, phenyl-HN—(C=O)—O—, and (phenyl$)_2$N—(C=O)—O—; and $R^{2b}$ and $R^{2c}$ taken together with the atoms to which they are attached form an optionally substituted mono-, bi- or polycyclic, saturated, unsaturated, or aromatic ring system optionally containing at least one heteroatom selected from the group consisting of N, O and S.

As used herein, the term "core fused heteroaromatic" refers to an optionally substituted heteroaromatic mono-, bi- or polycyclic ring system containing one or more heteroatoms selected from N, O and S; where the heteroaromatic ring system substituent is at least one independently selected from the group consisting of, but not limited to, hydrogen, halo, haloalkyl, $(C_1-C_6)$alkyl, $(C_2-C_6)$alkenyl, $(C_2-C_6)$alkynyl, perhalo$(C_1-C_6)$alkyl, $(C_5-C_{10})$heteroaryl, $(C_5-C_{10})$heterocyclic, $(C_3-C_{10})$cycloalkyl, hydroxy, $(C_1-C_6)$alkoxy, perhalo $(C_1-C_6)$alkoxy, phenoxy, $(C_5-C_{10})$heteroaryl-O—, $(C_5-C_{10})$heterocyclic-O—, $(C_3-C_{10})$cycloalkyl-O—, $(C_1-C_6)$alkyl-S—, $(C_1-C_6)$alkyl-$SO_2$—, $(C_1-C_6)$alkyl-NH—$SO_2$—, nitro, cyano, amino, $Ph(CH_2)_{1-6}NH$—, $(C_1-C_6)$alkylNH—, $(C_1-C_6)$alkylamino, [$(C_1-C_6)$alkyl$]_2$-amino, $(C_1-C_6)$alkyl-$SO_2$—NH—, amino(C=O)—, amino$SO_2$—, $(C_1-C_6)$alkyl-(C=O)—NH—, $(C_1-C_6)$alkyl-(C=O)—[$((C_1-C_6)$alkyl)-N]—, phenyl-(C=O)—NH—, phenyl-(C=O)—[$((C_1-C_6)$alkyl)-N]—, $(C_1-C_6)$alkyl-(C=O)—, phenyl-(C=O)—, $(C_5-C_{10})$heteroaryl-(C=O)—, $(C_5-C_{10})$heterocyclic-(C=O)—, $(C_3-C_{10})$cycloalkyl-(C=O)—, HO—(C=O)—, $(C_1-C_6)$alkyl-O—(C=O)—, $H_2N(C=O)$—$(C_1-C_6)$alkyl-NH—(C=O)—, [$(C_1-C_6)$alkyl$]_2$—N—(C=O)—, phenyl-NH—(C=O)—, phenyl-[$((C_1-C_6)$alkyl)-N]—(C=O)—, $(C_5-C_{10})$heteroaryl-NH—(C=O)—, $(C_5-C_{10})$heterocyclic-NH—(C=O)—, $(C_3-C_{10})$cycloalkyl-NH—(C=O)— and $(C_1-C_6)$alkyl-(C=O)—O—;

or any two adjacent core fused heteroaromatic substituents taken together with the carbons to which they are attached may form a 5-8 membered ring comprising at least one heteroatom selected from oxygen, sulfur or nitrogen; and wherein the alkyl groups and alkyl portions of the alkoxy or alkylamino groups may be straight chained or if comprised of at least three carbons may be branched or cyclic. Examples of a suitable core fused heteroaromatic include, but are not limited to,

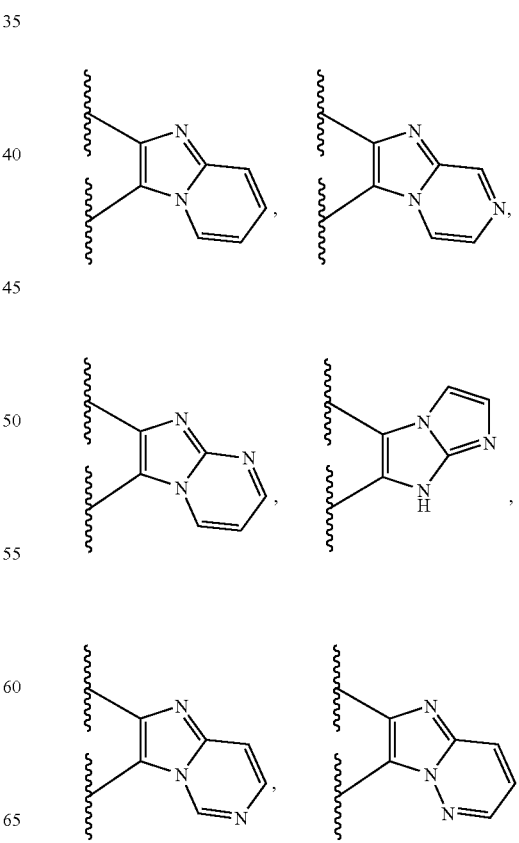

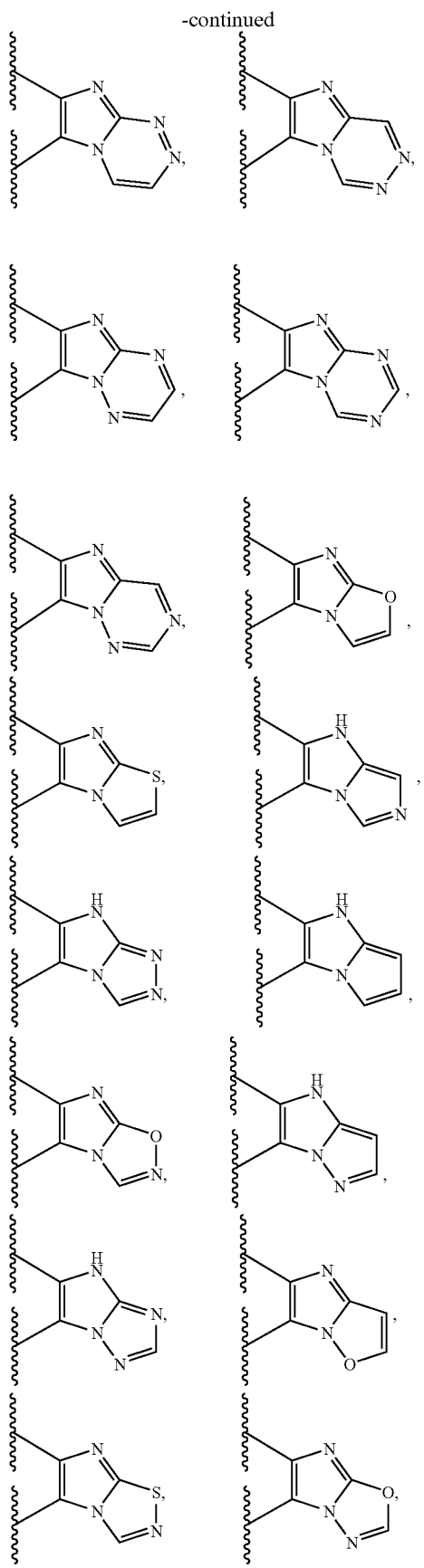
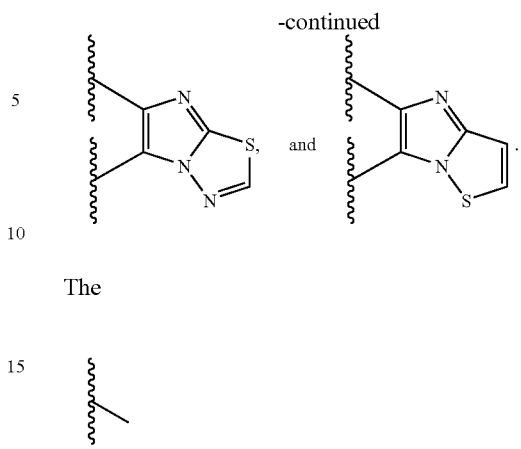

The moieties in the above illustrated core fused heteroaromatics represent a linkage to either R¹ or the 2-pyridyl moiety of formula (Ia) or (Ib). Other suitable examples of the core fused heteroaromatic include, but are not limited to the imidazole based "FusedHet" described in WO 03/000682.

DETAILED DESCRIPTION OF THE INVENTION

A compound of the invention may be prepared according to the following reaction schemes and discussion as well as those set forth in U.S. application Ser. Nos. 10/094,717, 10/094,760, and 10/115,952, and WO0240476, each of which is herein incorporated in its entirety by reference. Unless otherwise indicated, all variables in the reaction schemes and discussion that follow are each as defined herein.

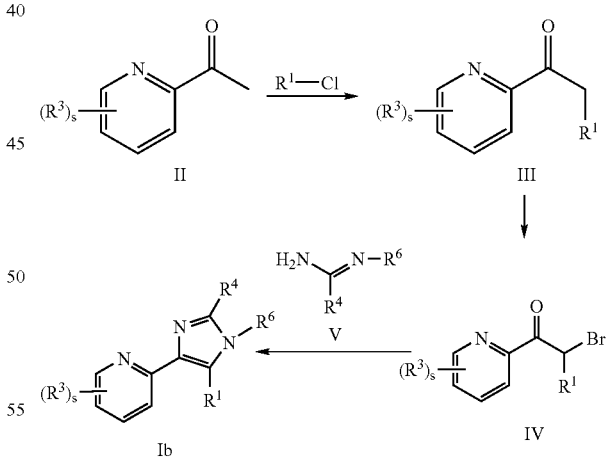

Scheme I refers to the preparation of compounds of the formula Ib. In Scheme I, R¹, R³, R⁴, R⁶, and s are each as defined above. Referring to Scheme 1, a compound of the formula III was prepared from compound of the formula II by reaction with an heteroaryl chloride of the formula R¹—Cl, in the presence of a catalyst such as palladium II acetate, a base, such as potassium tert-butoxide, and AMPHOS® (i.e., 2-dicyclohexylphosphino-2'-(N,N-dimethylamino)biphenyl, commercially available from Strem Chemicals, Newburyport, Mass.) in a polar aprotic solvent such as tetrahydrofuran. The aforesaid reaction was run at a temperature from about 50° C. to about 100° C., preferably 75° C., for a period from 6 hours to about 24 hours, preferably 18 hours.

The compound of formula IV was prepared from a compound of the formula III by reaction with $Br_2$ in a polar solvent. Suitable solvents included acetic acid, chloroform or methylene chloride, preferably acetic acid. The aforesaid reaction was conducted at a temperature of about 0° C. to about 30° C., preferably at about 22° C. (room temperature) for a period from about 10 minutes to about 4 hours, preferably about 30 minutes.

The compound of formula Ib was prepared from a compound of the formula IV by reaction with a compound of the formula V:

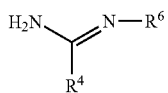
V wherein $R^4$ and $R^6$ are each as defined above, in a polar solvent. Suitable solvents include N,N'-dimethylformamide, N,N'-dimethylacetamide, dimethylsulfoxide, N-methylpyrrolidinone, methanol, ethanol, 1-propanol, 2-propanol, or tetrahydrofuran, preferably N,N'-dimethylformamide or ethanol. The aforesaid reaction was run at a temperature from about 50° C. to about 100° C., preferably 80° C., for a period from 1 hour to about 10 hours, preferably 4.5 hours.

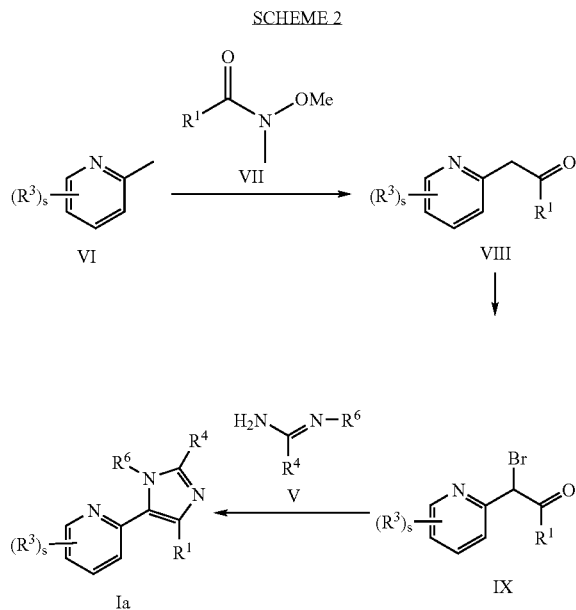

Scheme 2 refers to the preparation of compounds of the formula Ia. In Scheme 2, $R^1$, $R^3$, $R^4$, $R^6$, and s are each as defined above. Referring to Scheme 2, a compound of the formula VIII was prepared from a compound of the formula VI by treating with a base, such as butyl lithium, at a temperature of about -60° C. for a time period of about 90 minutes, followed by the slow addition of an amide of the formula VII, which is either commercially available or prepared according to Scheme 7, in a polar aprotic solvent, such as tetrahydrofuran. The aforesaid reaction was run at a temperature from about -78° C. to about 0° C., preferably -20° C., for a period from 1 hour to about 10 hours, preferably 3 hours.

The compound of formula IX was prepared from a compound of the formula VIII according to the procedure described in Scheme 1 for the conversion of compounds of the formula III to compounds of the formula IV.

The compound of the formula Ia was prepared from a compound of the formula IX according to the procedure described in Scheme 1 for the conversion of compounds of the formula IV to compounds of the formula Ib.

SCHEME 3

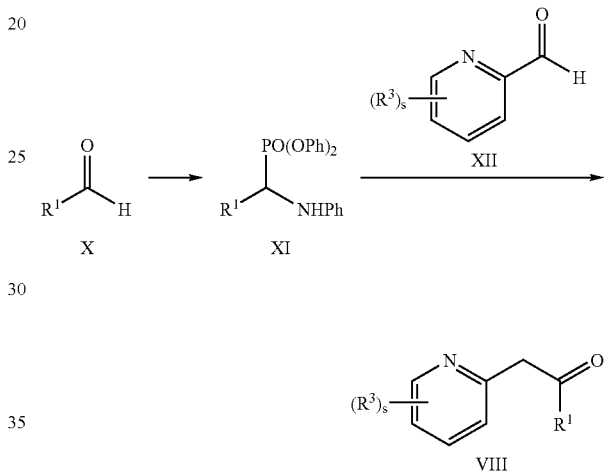

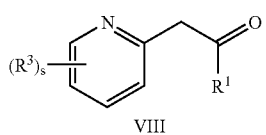

Scheme 3 refers to the preparation of compounds of the formula VIII, which are intermediates useful in the preparation of compounds of the formula Ia in Scheme 2. In Scheme 3, $R^1$, $R^3$ and s are each as defined above. Referring to Scheme 3, compounds of the formula XI were prepared from aldehydes of the formula X by first treatment with an aromatic amine, such as aniline, in a polar solvent. Suitable solvents include ethyl acetate, isopropyl acetate, or tetrahydrofuran, preferably isopropyl acetate. The resulting reaction mixture is heated to a temperature from about 50° C. to about 100° C., preferably 60° C., and then slowly treated with phosphorous acid diphenyl ester. The 60° C. temperature of the reaction mixture was maintained for a period from 30 minutes to about 3 hours, preferably 1 hour and then cooled to ambient temperature overnight.

A compound of the formula VIII was prepared from a compound of the formula XI by reaction with a pyridine aldehyde of the formula XII in the presence of a base, such as potassium tert-butoxide, in a polar solvent. Suitable solvents include ethyl acetate, isopropyl acetate, or tetrahydrofuran, preferably a mixture of tetrahydrofuran and isopropyl acetate. The aforesaid reaction was run at a temperature from about 0° C. to about 100° C., preferably 22° C. (ambient temperature), for a period from 30 minutes to about 5 hours, preferably 2 hours. The resulting reaction mixture was then treated with acid, such as hydrochloric acid for a period from 30 minutes to about 5 hours, preferably 1 hour.

A compound of the formula X was prepared according to Scheme 5.

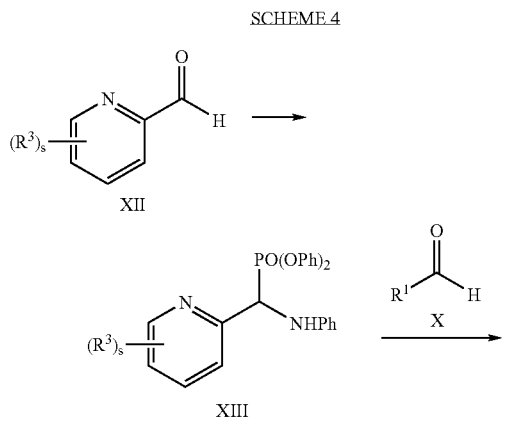

Scheme 4 refers to the preparation of compounds of the formula III, which are intermediates useful in the preparation of compounds of the formula Ib in Scheme 1. In Scheme 4, $R^1$, $R^3$ and s are each as defined above. Referring to Scheme 4, compounds of the formula XIII were prepared from pyridine aldehydes of the formula XII according to the procedure described in Scheme 3 for the preparation of a compound of the formula XI from a compound of the formula X. A compound of the formula X was prepared according to Scheme 5.

A compound of the formula III was prepared from a compound of the formula XIII according to the procedure described in Scheme 3 for the preparation of a compound of the formula VIII from a compound of the formula XI.

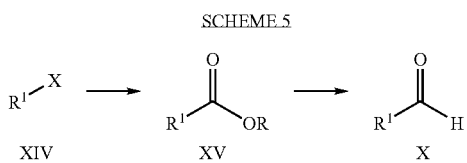

Scheme 5 refers to the preparation of compounds of the formula X, which are intermediates useful in the preparation of compounds of the formula VIII and III in Scheme 3 and Scheme 4, respectively. In Scheme 5, $R^1$ is as defined above and R is a simple alkyl group such as methyl or ethyl. Referring to Scheme 5, compounds of the formula XV were prepared from heteroarylhalides of the formula, XIV, wherein X is a chloride or bromide, by an alkoxycarbonylation reaction. Suitable conditions include metal-halogen exchange with butyl lithium in a solvent such as tetrahydrofuran at a temperature about 0° C., for a period of time of about 30 minutes, followed by the addition of ethylchloroformate at a temperature of about 0° C., followed by a period of time of about 2.4 hours at about 50° C.

The compound of the formula X was prepared from a compound of the formula XV with a two-step process. First the compound of formula XV was treated with a reducing agent. Suitable reducing agents include lithium borohydride, sodium borohydride, lithium aluminum hydride, and borane in tetrahydrofuran. Suitable solvents include methanol, ethanol, tetrahydrofuran, diethyl ether, and dioxane. The aforesaid reaction was run at a temperature from about 0° C. to about 100° C., preferably 65° C., for a period from 10 minutes to about 1 hour, preferably 30 minutes. The resulting primary alcohol was then oxidized to the corresponding aldehyde of the formula X by treating with an oxidizing agent, such as N-methyl morpholine N-oxide/TPAP, Dess-Martin reagent, PCC or oxalyl chloride-DMSO, preferably oxalyl chloride-DMSO. Suitable solvents for the aforesaid reaction include chloroform, tetrahydrofuran, or dichloromethane. The aforesaid reaction was conducted at a temperature from about −78° C. to about 22° C. for a time from about 15 minutes to about 3 hours, preferably about 1 hour.

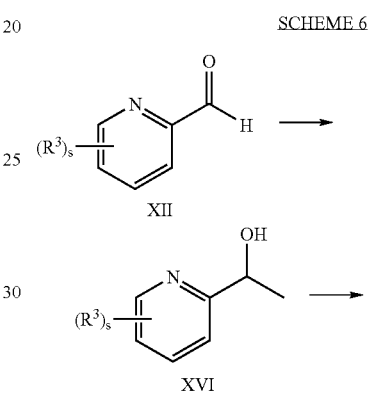

Scheme 6 refers to the preparation of compounds of the formula II, which are intermediates useful in the preparation of compounds of the formula Ib in Scheme 1. In Scheme 6, $R^3$ and s are each as defined above. Referring to Scheme 6, a compound of formula XVI was prepared from a compound of the formula XII by reaction with methyl magnesium bromide in a polar solvent such as a mixture of tetrahydrofuran and toluene. The aforesaid reaction was run at a temperature from about −78° C. to about 0° C., preferably −60° C., for a period from 10 minutes to about 1 hour, preferably 40 minutes, followed by a period of about 90 minutes at a temperature of about −10° C.

The compound of formula II was prepared from a compound of the formula XVI by treating with an oxidizing agent, such as N-methyl morpholine N-oxide/TPAP, Dess-Martin reagent, PCC or oxalyl chloride-DMSO, preferably oxalyl chloride-DMSO. Suitable solvents for the aforesaid reaction include chloroform, tetrahydrofuran, or dichloromethane. The aforesaid reaction was conducted at a temperature from about −78° C. to about 22° C. for a time from about 15 minutes to about 3 hours, preferably about 1 hour.

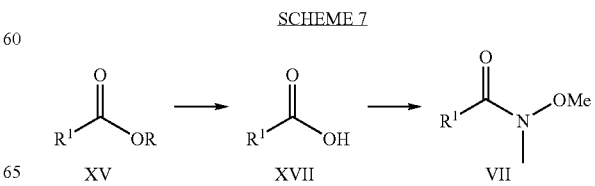

Scheme 7 refers to the preparation of compounds of the formula VII, which are intermediates useful in the preparation of compounds of the formula Ia in Scheme 2. In Scheme 7, $R^1$ is as defined above and R is a simple alkyl group such as methyl or ethyl. Referring to Scheme 7, compounds of the formula XVII were prepared from a compound of the formula XV, which may be prepared according to a procedure described in Scheme 5, by treatment with a base such as lithium hydroxide, in a polar protic solvent. Suitable solvents for the aforesaid reaction included methanol, ethanol, and water. The aforesaid reaction was conducted at a temperature from about 0° C. to about 30° C. preferably about 22° C. (room temperature) for a time from about 15 minutes to about 3 hours, preferably about 1 hour.

The compound of the formula VII was prepared from a compound of the formula XVII by reaction with a suitable activating agent and a compound of the formula

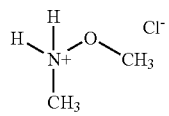

and a base. Suitable activating agents included thionyl chloride, carbonyldiimidazole, EDCI and DCC, preferably oxalyl chloride. Suitable bases included triethylamine, Hunig's base, or DBU, preferably triethylamine. Suitable solvents for the aforesaid reaction include methylene chloride, N,N'-dimethylformamide, tetrahydrofuran, and a mixture thereof, preferably methylene chloride. The aforesaid reaction was conducted at a temperature from about 0° C. to about 30° C., preferably about 22° C. (room temperature) for a time from about 6 hours to about 48 hours, preferably about 12 hours.

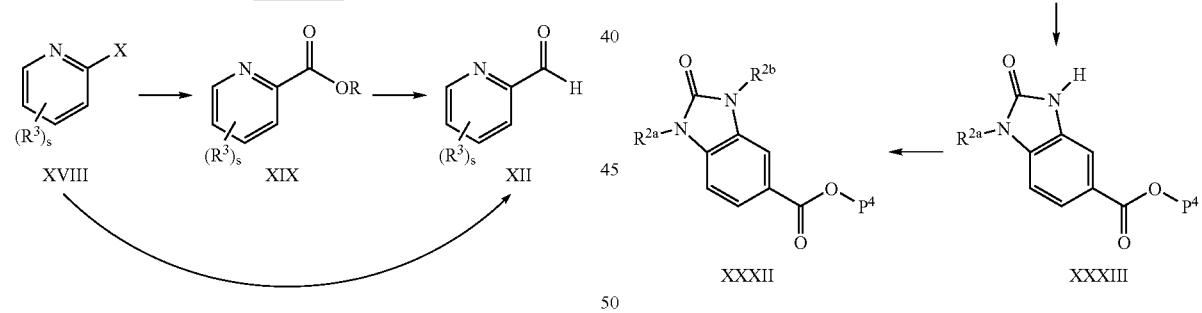

Scheme 8 refers to the preparation of compounds of the formula XII, which are intermediates useful in the preparation of compounds of the formula VIII, III, and II in Scheme 3, Scheme 4 and Scheme 6, respectively. In Scheme 8, $R^3$ and s are each as defined above, R is a simple alkyl group such as methyl or ethyl, and X is a halo such as chloro or bromo. Referring to Scheme 8, compounds of the formula XIX were prepared from heteroarylhalides of the formula XVIII according to the procedure described in Scheme 5 for the preparation of a compound of the formula XV from a compound of the formula XIV.

The compound of the formula XII was prepared from a compound of the formula XIX according to a two-step process described in Scheme 5 for the preparation of a compound of the formula X from a compound of the formula XV. Alternatively, a compound of the formula XII may be prepared directly from a heteroarylhalides of the formula, XVIII, wherein X is a chloride or bromide, by a formylation reaction. Suitable conditions include metal-halogen exchange with isopropyl magnesium bromide in a solvent such as tetrahydrofuran at a temperature about 0° C., for a period of time of about 30 minutes, followed by the addition of N,N'-dimethylformamide at a temperature of about 0° C., followed by a period of time of about 2.4 hours at about 50° C.

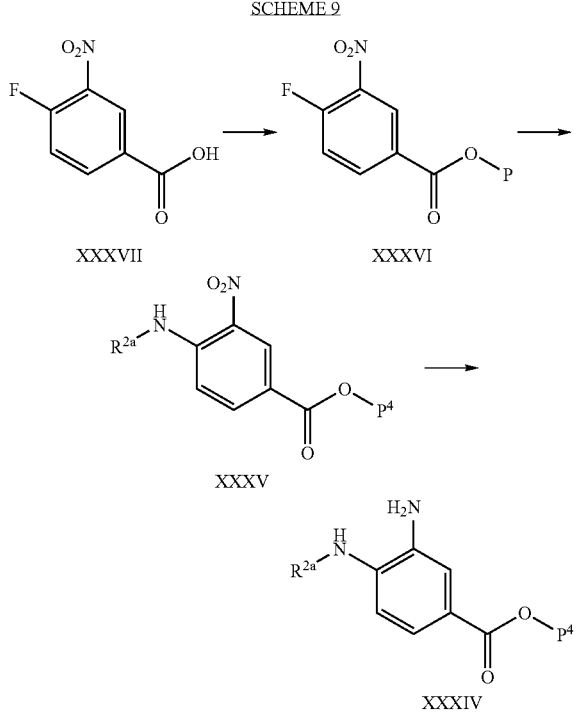

Scheme 9 refers to the preparation of compounds of formula XXXII. In Scheme 9, $R^{2a}$ and $R^{2b}$ are each as defined above. The compound of formula XXXII, wherein $P^4$ is $(C_1-C_6)$alkyl, was prepared from a compound of formula XXXIII, wherein $P^4$ is $(C_1-C_6)$alkyl, by reaction with an alkylating reagent of the formula $R^{2b}L$, wherein L is a leaving group such as iodo and bromo, in the presence of a base. Suitable bases included sodium hydride and cesium carbonate. Suitable solvents included dimethyl sulfoxide, N,N'-dimethylformamide. The aforesaid reaction was conducted at a temperature from about 0° C. to about 30° C., preferably about 22° C., for a period from about 10 minutes to about 2 hours, preferably about 1 hour.

The compound of formula XXXIII, wherein $P^4$ is $(C_1-C_6)$alkyl, was prepared from a compound of formula XXXIV, wherein $P^4$ is $(C_1-C_6)$alkyl, by reaction with a phosgene equivalent. Suitable phosgene equivalents included phosgene, triphosgene and carbonyldiimidazole. Suitable solvents included dichloromethane, THF, benzene and dichloroethane. The aforesaid reaction was run at a temperature from about 10° C. to about 30° C., preferably at about 22° C. (room temperature) for a period from about 10 minutes to about 2 hours, preferably about 30 minutes.

The compound of formula XXXIV was prepared from a compound of formula XXXV by reaction with a reducing agent using standard techniques that are well known to those skilled in the art. For example, reduction may be effected with hydrogen gas ($H_2$), using catalysts such as palladium on carbon (Pd/C), palladium on barium sulfate ($Pd/BaSO_4$), platinum on carbon (Pt/C), or tris(triphenylphosphine) rhodium chloride (Wilkinson's catalyst), as described in *Catalytic Hydrogenation in Organic Synthesis*, Paul Rylander, Academic Press Inc., San Diego, 31-63 (1979). Suitable solvents include methanol, ethanol, THF, dioxane or ethyl acetate, at a pressure from about 1 to about 5 atmospheres. The aforesaid reaction was run at a temperature from about 10° C. to about 60° C., preferably about 22° C. (room temperature), for a period from about 1 hour to about 3 hours, preferably about 2 hours. The following conditions are preferred: 10% palladium on carbon, ethanol at 22° C. and 50 psi of hydrogen gas pressure.

The compound of formula XXXV was prepared from a compound of formula XXXVI by reaction with an amine of the formula $R^{2a}NH_2$ in the presence of a base. Suitable bases include the amine of the formula $R^{2a}NH_2$, triethylamine and dimethylaminopyridine, preferably the base was the amine of the formula $R^{2a}NH_2$. Suitable solvents include dichloromethane, chloroform, dichloroethane and THF, preferably dichloromethane. The aforesaid reaction was run at a temperature from about 0° C. to about 30° C., preferably 22° C. (room temperature) for a period from about 6 hours to about 48 hours, preferably about 12 hours.

The compound of formula XXXVI, wherein $P^4$ is ($C_1$-$C_6$) alkyl, was prepared from a compound of formula XXXVII by reaction with an activating reagent, an alcohol and a base. Suitable activating agents include oxalyl chloride with catalytic N,N'-dimethylformamide, thionyl chloride, and carbodiimide. Suitable alcohols include methanol, ethanol or propanol. Suitable bases include triethylamine or diisopropylethylamine. The aforesaid reaction was conducted at a temperature of about −10° C. to about 5° C., preferably at about 0° C., for a period from about 1 hour to about 3 hours, preferably 2 hours.

The compound of the formula XXXVII can be prepared by methods well known to those skilled in the art.

SCHEME 10

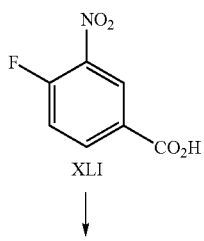

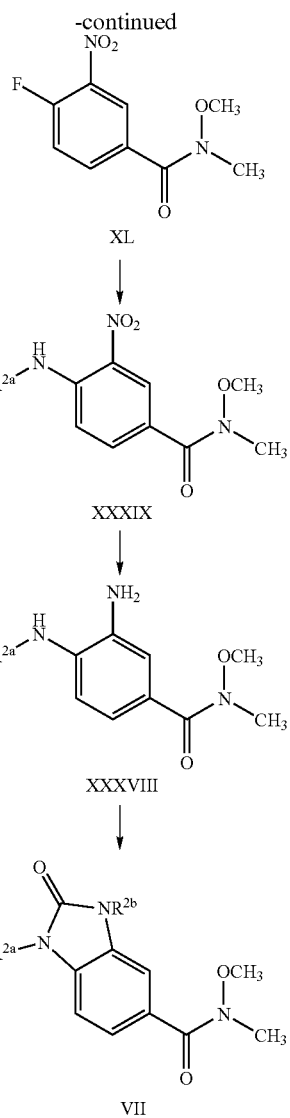

Scheme 10 refers to the preparation of compounds of the formula VII, which are intermediates useful in the preparation of compounds of formula (Ia) and (Ib), each as set forth above. In Scheme 10, $R^{2a}$ and $R^{2b}$ are each as defined above. Referring to Scheme 10, a compound of the formula VII was prepared from a compound of the formula XXXVIII according to the procedure described in Scheme 9 for the preparation of a compound of the formula XXXIII from a compound of the formula XXXIV.

The compound of formula XXXVIII can be prepared from compounds of the formula XXXIX by hydrogenation conditions such as described in Scheme 9 for the conversion of compounds of formula XXXV to compounds of the formula XXXIV.

Compounds of the formula XXXIX can be prepared from compounds of the formula XL according to conditions such as described in Scheme 9 for the conversion of compounds of formula XXXVI to compounds of the formula XXXV.

Compounds of the formula XL can be prepared from compounds of the formula XLI according to the procedure described in Scheme 7 for the preparation of a compound of the formula VII from a compound of the formula XVII.

Compounds of the formula XLI and XLII are commercially available or can be made by methods well known to those skilled in the art.

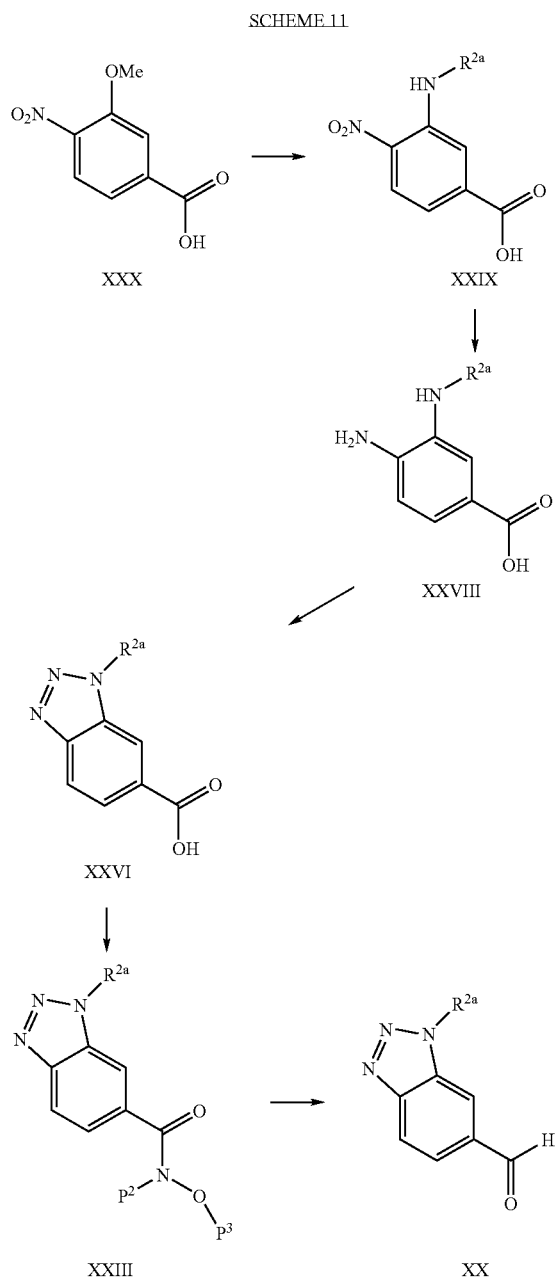

SCHEME 11

Scheme 11 refers to the preparation of compounds of the formula XX and XXIII, both are intermediates useful in the preparation of compounds of formula (Ia) and (Ib), each as set forth above. In Scheme 11, $R^{2a}$ is as defined above. Referring to Scheme 11, a compound of the formula XX was prepared from a compound of formula XXIII by reaction with a reducing agent, such as diisobutylaluminum hydride (DIBAL) in toluene, in a solvent, such as tetrahydrofuran (THF). The aforesaid reaction may be run at a temperature from about −78° C. to room temperature for a period from about one to about five hours.

The compound of formula XXIII was prepared from a compound of formula XXVI according to the procedure described in Scheme 7 for the preparation of a compound of the formula VII from a compound of the formula XVII.

The compound of formula XXVI was prepared from a compound of formula XXVIII by reaction with sodium nitrite under acidic conditions. Suitable acids include hydrochloric acid. The aforesaid reaction was conducted at a temperature from about 0° C. to about 100° C., preferably about 22° C., for a period from about 1 hour to about 3 hours, preferably about 2 hours.

The compound of formula XXVIII was prepared from a compound of formula XXIX by reaction with a reducing agent as described in Scheme 10 for the preparation of a compound of the formula XXXVIII from a compound of the formula XXXIX.

The compound of formula XXIX can be prepared from a compound of formula XXX by reaction with an amine of the formula $R^{2a}NH_2$. Suitable solvents include an excess of the amine reactant (neat), glyme, and toluene, preferably neat. The aforesaid reaction was conducted at a temperature from about 70° C. to about 120° C., preferably 100° C., for a period from about 10 minutes to about 1 hour, preferably about 30 minutes.

The compound of the formula XXX is commercially available or can be prepared by methods well known to those skilled in the art.

SCHEME 12

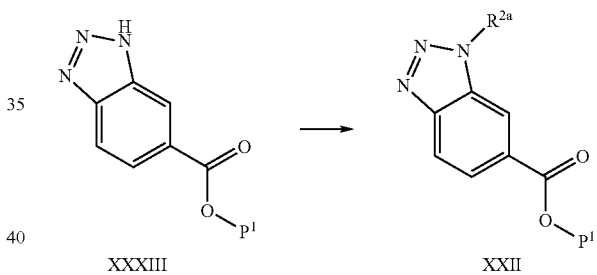

Scheme 12 refers to the preparation of compounds of the formula XXII, which is an intermediate useful in the preparation of compounds of formula (Ia) and (Ib), each as set forth above. In Scheme 12, $R^{2a}$ is as defined above and $P^1$ is $(C_1$-$C_6)$alkyl. The compound of formula XXII was prepared from a compound of formula XXXIII according to the procedure described in Scheme 9 for the preparation of a compound of the formula XXXII from a compound of the formula XXXIII.

Compounds of the formula XXXIII are commercially available or can be made by methods well known to those of ordinary skill in the art.

SCHEME 13

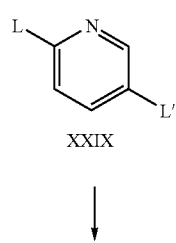

XXIX

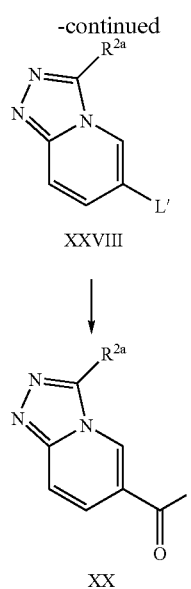

Scheme 13 refers to the preparation of compounds of the formula XX, which is an intermediate useful in the preparation of compounds of formula (Ia) and (Ib), each as set forth above. In Scheme 13, $R^{2a}$ is as defined above. Compounds of formula XX were prepared from compounds of formula XXVIII by a formylation reaction. Suitable conditions for formylation include metal-halogen exchange with isopropylmagnesium chloride in a solvent such as tetrahydrofuran at a temperature of about 0° C., for a period of time of about 30 minutes, followed by the addition of N,N'-dimethylformamide at a temperature of about 0° C., followed by a period of time of about 2.5 hours at a temperature of about 50° C.

Compounds of formula XXVIII were prepared as described in the literature (Moran, D. B.; Morton, G. O.; Albright, J. D., *J. Heterocycl. Chem.*, Vol. 23, pp. 1071-1077 (1986)) or from compounds of formula XXIX wherein L' is bromo or fluoro. Compounds of formula XXIX are commercially available.

All pharmaceutically acceptable salts, tautomers, prodrugs, hydrates and solvates of a compound of the invention is also encompassed by the invention.

A compound of the invention which is basic in nature is capable of forming a wide variety of different salts with various inorganic and organic acids. Although such salts must be pharmaceutically acceptable for administration to animals and humans, it is often desirable in practice to initially isolate a compound of the invention from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as, for example, methanol or ethanol. Upon careful evaporation of the solvent, the desired solid salt is obtained.

The acids which can be used to prepare the pharmaceutically acceptable acid addition salts of the base compounds of this invention are those which form non-toxic acid addition salts, i.e., salts containing pharmacologically acceptable anions, such as chloride, bromide, iodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

A compound of the invention which is also acidic in nature, e.g., contains a COOH or tetrazole moiety, is capable of forming base salts with various pharmacologically acceptable cations. Although such salts must be pharmaceutically acceptable for administration to animals and humans, it is often desirable in practice to initially isolate a compound of the invention from the reaction mixture as a pharmaceutically unacceptable salt (e.g., lithium salts) which can be easily isolated and then converted later to a pharmaceutically acceptable base addition salt. Examples of such pharmaceutically acceptable base addition salts include the alkali metal or alkaline-earth metal salts and particularly, the sodium and potassium salts. These salts can be prepared by conventional techniques. The chemical bases which can be used as reagents to prepare the pharmaceutically acceptable base addition salts of this invention are those which form non-toxic base salts with the herein described acidic compounds of the invention. These non-toxic base salts include but are not limited to salts derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

Isotopically-labeled compounds are also encompassed by the present invention. As used herein, an "isotopically-labeled compound" refers to a compound of the invention including pharmaceutical salts, prodrugs thereof, each as described herein, in which one or more atoms are replaced by an atom having an atomic mass or mass number different from the atomic mass or mass number usually found in nature. Examples of isotopes that can be incorporated into compounds of the invention include but are not limited to isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

By isotopically-labeling a compound of the present invention, the compounds may be useful in drug and/or substrate tissue distribution assays. Tritiated ($^{3}H$) and carbon-14 ($^{14}C$) labeled compounds are particularly preferred for their ease of preparation and detectability. Further, substitution with heavier isotopes such as deuterium ($^{2}H$) can afford certain therapeutic advantages resulting from greater metabolic stability, for example increased in vivo half-life or reduced dosage requirements and, hence, may be preferred in some circumstances. Isotopically labeled compounds of the invention, including pharmaceutical salts, prodrugs thereof, can be prepared by any means known in the art.

Stereoisomers (e.g., cis and trans isomers) and all optical isomers of a compound of the invention (e.g., R and S enantiomers), as well as racemic, diastereomeric and other mixtures of such isomers are contemplated by the present invention.

The compounds, salts, prodrugs, hydrates, and solvates of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds.

The present invention also includes atropisomers of the present invention. Atropisomers refer to compounds of the invention that can be separated into rotationally restricted isomers.

A compound of the invention, as described above, can be used in the manufacture of a medicament for the prophylactic or therapeutic treatment of a TGF-related disease state in an animal or human.

A compound of the invention is a potent inhibitor of transforming growth factor ("TGF")-β signaling pathway and are therefore of use in therapy. Accordingly, the present invention provides a method of preventing or treating a TGF-related disease in an animal or human comprising the step of administering a therapeutically effective amount of at least one compound of the invention to the animal or human suffering from the TGF-related disease state.

As used herein, the term "therapeutically effective amount" refers to an amount of a compound of the invention required to inhibit the TGF-β signaling pathway. As would be understood by one of skill in the art, a "therapeutically effective amount" will vary from patient to patient and will be determined on a case by case basis. Factors to consider include, but are not limited to, the patient being treated, weight, health, compound administered, etc.

There are numerous disease states that can be treated by inhibition of the TGF-β signaling pathway. Such disease states include, but are not limited to, all types of cancer (e.g., breast, lung, colon, prostate, ovarian, pancreatic, melanoma, all hematological malignancies, etc.) as well as all types of fibrotic diseases (e.g., glomerulonephritis, diabetic nephropathy, hepatic fibrosis, pulmonary fibrosis, arterial hyperplasia and restenosis, scleroderma, and dermal scarring).

The present invention also provides a pharmaceutical composition containing at least one compound of the invention and at least one pharmaceutically acceptable carrier. The pharmaceutically acceptable carrier may be any such carrier known in the art including those described in, for example, Remington's Pharmaceutical Sciences, Mack Publishing Co., (A. R. Gennaro edit. 1985). A pharmaceutical composition of the invention may be prepared by conventional means known in the art including, for example, mixing at least one compound of the invention with a pharmaceutically acceptable carrier.

A pharmaceutical composition of the invention may be used in the prevention or treatment of a TGF-related disease state, as described above, in an animal or human. Thus, a compound of the invention may be formulated as a pharmaceutical composition for oral, buccal, intranasal, parenteral (e.g., intravenous, intramuscular or subcutaneous), topical, or rectal administration or in a form suitable for administration by inhalation or insufflation.

For oral administration, the pharmaceutical composition may take the form of, for example, a tablet or capsule prepared by conventional means with a pharmaceutically acceptable excipient such as a binding agent (e.g., pregelatinized maize starch, polyvinylpyrrolidone or hydroxypropyl methylcellulose); filler (e.g., lactose, microcrystalline cellulose or calcium phosphate); lubricant (e.g., magnesium stearate, talc or silica); disintegrant (e.g., potato starch or sodium starch glycolate); or wetting agent (e.g., sodium lauryl sulphate).

The tablets may be coated by methods well known in the art. Liquid preparations for oral administration may take the form of a, for example, solution, syrup or suspension, or they may be presented as a dry product for constitution with water or other suitable vehicle before use. Such liquid preparations may be prepared by conventional means with a pharmaceutically acceptable additive such as a suspending agent (e.g., sorbitol syrup, methyl cellulose or hydrogenated edible fats); emulsifying agent (e.g., lecithin or acacia); non-aqueous vehicle (e.g. almond oil, oily esters or ethyl alcohol); and preservative (e.g., methyl or propyl p-hydroxybenzoates or sorbic acid).

For buccal administration, the composition may take the form of tablets or lozenges formulated in conventional manner.

A compound of the present invention may also be formulated for sustained delivery according to methods well known to those of ordinary skill in the art. Examples of such formulations can be found in U.S. Pat. Nos. 3,538,214, 4,060,598, 4,173,626, 3,119,742, and 3,492,397, which are herein incorporated by reference in their entirety.

A compound of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain a formulating agent such as a suspending, stabilizing and/or dispersing agent. Alternatively, the active ingredient may be in powder form for reconstitution with a suitable vehicle, e.g., sterile pyrogen-free water, before use.

A compound of the invention may also be formulated in rectal compositions such as suppositories or retention enemas, e.g., containing conventional suppository bases such as cocoa butter or other glycerides.

For intranasal administration or administration by inhalation, a compound of the invention may be conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the compound of the invention. Capsules and cartridges (made, for example, from gelatin) for use in an inhaler or insufflator may be formulated containing a powder mix of a compound of the invention and a suitable powder base such as lactose or starch.

A proposed dose of a compound of the invention for oral, parenteral or buccal administration to the average adult human for the treatment of a TGF-related disease state is about, 0.1 mg to about 2000 mg, preferably about 0.1 mg to about 200 mg of the active ingredient per unit dose which could be administered, for example, 1 to 4 times per day.

Aerosol formulations for treatment of the conditions referred to above in the average adult human are preferably arranged so that each metered dose or "puff" of aerosol contains about 20 kg to about 10,000 µg, preferably, about 20 µg to about 1000 µg of a compound of the invention. The overall daily dose with an aerosol will be within the range of about 100 µg to about 100 mg, preferably, about 1100 µg to about 10 mg. Administration may be several times daily, for example 2, 3, 4 or 8 times, giving for example, 1, 2 or 3 doses each time.

Aerosol combination formulations for treatment of the conditions referred to above in the average adult human are preferably arranged so that each metered dose or "puff" of aerosol contains from about 0.01 mg to about 1000 mg, preferably, from about 0.01 mg to about 100 mg of a compound of this invention, more preferably from about 1 mg to about 10 mg of such compound. Administration may be several times daily, for example 2, 3, 4 or 8 times, giving for example, 1, 2 or 3 doses each time.

Aerosol formulations for treatment of the conditions referred to above in the average adult human are preferably arranged so that each metered dose or "puff" of aerosol contains from about 0.01 mg to about 20,000 mg, preferably, about 0.01 mg to about 2000 mg of a compound of the invention, more preferably from about 1 mg to about 200 mg. Administration may be several times daily, for example 2, 3, 4 or 8 times, giving for example, 1, 2 or 3 doses each time.

For topical administration, a compound of the invention may be formulated as an ointment or cream.

This invention also encompasses pharmaceutical compositions containing and methods of treatment or prevention comprising administering prodrugs of at least one compound of the invention. As used herein, the term "prodrug" refers to a pharmacologically inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo, when they undergo solvolysis under physiological conditions or undergo enzymatic degradation. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, Calif., 1992). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability. For example, a compound of the invention having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of the invention. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters which are covalently bonded to the above substituents of a compound of the invention through the carbonyl carbon prodrug sidechain.

According to the invention, in the treatment of a TGF-related disease state, a compound of the invention, as described herein, whether alone or as part of a pharmaceutical composition may be combined with another compound(s) of the invention and/or with another therapeutic agent(s). Examples of suitable therapeutic agent(s) include, but are not limited to, standard non-steroidal anti-inflammatory agents (hereinafter NSAID's) (e.g., piroxicam, diclofenac), propionic acids (e.g., naproxen, flubiprofen, fenoprofen, ketoprofen and ibuprofen), fenamates (e.g., mefenamic acid, indomethacin, sulindac, apazone), pyrazolones (e.g., phenylbutazone), salicylates (e.g., aspirin), COX-2 inhibitors (e.g., celecoxib, valdecoxib, rofecoxib and etoricoxib), analgesics and intraarticular therapies (e.g., corticosteroids) and hyaluronic acids (e.g., hyalgan and synvisc), anticancer agents (e.g., endostatin and angiostatin), cytotoxic drugs (e.g., adriamycin, daunomycin, cis-platinum, etoposide, taxol, taxotere),alkaloids (e.g., vincristine), and antimetabolites (e.g., methotrexate), cardiovascular agents (e.g., calcium channel blockers), lipid lowering agents (e.g., statins), fibrates, beta-blockers, Ace inhibitors, Angiotensin-2 receptor antagonists and platelet aggregation inhibitors, CNS agents (e.g., as antidepressants (such as sertraline)), anti-Parkinsonian drugs (e.g., deprenyl, L-dopa, Requip, Mirapex), MAOB inhibitors (e.g., selegine and rasagiline), comP inhibitors (e.g., Tasmar), A-2 inhibitors, dopamine reuptake inhibitors, NMDA antagonists, Nicotine agonists, Dopamine agonists and inhibitors of neuronal nitric oxide synthase), anti-Alzheimer's drugs (e.g., donepezil, tacrine, COX-2 inhibitors, propentofylline or metryfonate), osteoporosis agents (e.g., roloxifene, droloxifene, lasofoxifene or fosomax), and immunosuppressant agents (e.g., FK-506 and rapamycin).

Biological Activity

The activity of the compounds of the invention for the various TGF-related disease states as described herein can be determined according to one or more of the following assays. According to the invention, a compound of the invention exhibits an in vitro $IC_{50}$ value of up to about 10 μM. For example, the compound of Example 15 exhibits an in vitro $IC_{50}$ value against TβRI of 253 nM.

The compounds of the present invention also possess differential activity (i.e. are selective for) for TβRI over TβRII and TβRIII. Selectivity is measured in standard assays as a $IC_{50}$ ratio of inhibition in each assay.

TGF-β Type II Receptor (TβRII) Kinase Assay Protocol

Phosphorylation of myelin basic protein (MBP) by the TβR$^{11}$ kinase was measured as follows: 80 microliters of MBP (Upstate Biotechnology #13-104) diluted in kinase reaction buffer (KRB) containing 50 mM MOPS, 5 mM $MgCl_2$, pH 7.2 to yield a final concentration of 3 micromolar MBP was added to each well of a Millipore 96-well multiscreen-DP 0.65 micron filtration plate (#MADPNOB50). 20 microliters of inhibitor diluted in KRB was added to appropriate wells to yield the desired final concentration (10-0.03 micromolar). 10 microliters of a mixture of ATP (Sigma #A-5394) and $^{33}$P-ATP (Perkin Elmer #NEG/602H) diluted in KRB was added to yield a final concentration of 0.25 micromolar ATP and 0.02 microcuries of $^{33}$P-ATP per well. 10 microliters of a GST-TβRII fusion protein (glutathione S-transferase at the N-terminal end of the cytoplasmic domain of TβRII-amino acids 193-567 with A to V change at 438) diluted in KRB was added to each well to yield a final concentration of 27 nanomolar GST-TβRII. Plates were mixed and incubated for 90 minutes at room temperature. After the reaction incubation, 100 microliters of cold 20% trichloroacetic acid (Aldrich #25,139-9) was added per well and plates were mixed and incubated for 60 minutes at 4° C. Liquid was then removed from the wells using a Millipore vacuum manifold. Plates were washed once with 200 microliters per well of cold 10% trichloroacetic acid followed by two washes with 100 microliters per well of cold 10% trichloroacetic acid. Plates were allowed to dry overnight at room temperature. 20 microliters of Wallac OptiPhase SuperMix scintillation cocktail was added to each well. Plates were sealed and counted using a Wallac 1450 Microbeta liquid scintillation counter. The potency of inhibitors was determined by their ability to reduce TβRII-mediated phosphorylation of the MBP substrate.

ALK-5 (TβRI) Kinase Assay Protocol

The kinase assays were performed with 65 nM GST-ALK5 and 84 nM GST-Smad3 in 50 mM HEPES, 5 mM $MgCl_2$, 1 mM $CaCl_2$, 1 mM dithiothreitol, and 3_M ATP. Reactions were incubated with 0.5_Ci of [33 P]ATP for 3 h at 30° C. Phosphorylated protein was captured on P-81 paper (Whatman, Maidstone, England), washed with 0.5% phosphoric acid, and counted by liquid scintillation. Alternatively, Smad3 or Smad1 protein was also coated onto FlashPlate Sterile Basic Microplates (PerkinElmer Life Sciences, Boston, Mass.). Kinase assays were then performed in FlashPlates with same assay conditions using either the kinase domain of ALK5 with Smad3 as substrate or the kinase domain of ALK6 (BMP receptor) with Smad1 as substrate. Plates were washed three times with phosphate buffer and counted by TopCount (Packard Bio-science, Meriden, Conn.). (Laping, N. J. et al. *Molecular Pharmacology* 62:58-64 (2002)).

The following Examples illustrate the preparation of the compounds of the present invention. Unless indicated otherwise, all reagents are commercially available from vendors such as, for example, Aldrich. One of ordinary skill in the art will appreciate that in some cases protecting groups may be required during preparation. After the target molecule is made, the protecting group can be removed by methods well known to those of ordinary skill in the art, such as described in Greene and Wuts, "Protective Groups in Organic Synthesis" ($2^{nd}$ Ed, John Wiley & Sons 1991).

Analytical high performance liquid chromatography on reverse phase with mass spectrometry detection (LCMS) was done using Polaris 2×20 mm C18 column. Gradient elution was applied with increase of concentration of acetonitrile in 0.01% aqueous formic acid from 5% to 100% during 3.75 min period. Mass spectrometer Micromass ZMD was used for molecular ion identification.

EXAMPLE 1

Preparation of 2-Benzo[1,3]dioxol-5-yl-3-(6-methyl-pyridin-2-yl)-imidazo[1,2-a]pyrimidine Step A: Preparation of Benzo[1,3]dioxole-5-carboxylic acid methoxy-methyl-amide To a solution of benzo[1,3]dioxole-5-carboxylic acid (69 g, 415 mmol) in dimethylformamide (1L) was added di-imidazol-1-yl-methanone (74 g, 1.1 equiv), and the resulting reaction mixture was stirred at ambient temperature for 90 minutes. N,O-Dimethyl-hydroxylamine (43 g, 1.1 equiv) was added to the reaction mixture. The resulting reaction mixture was stirred at ambient temperature for 18 hours, and then concentrated in vacuo to ¼ of the volume, poured into 5% aqueous sodium hydrogen carbonate (1L), stirred at ambient temperature for 20 minutes, and then extracted with methyl tert-butyl ether (2×300 mL). The combined organics extracts were dried over magnesium sulfate and concentrated in vacuo. The resulting residue was azeotroped with toluene (800 mL) and dried under vacuum for 3 hours. The crude product was used in the next step without further purification.

Step B: Preparation of 1-Benzo[1,3]dioxol-5-yl-2-(6-methyl-pyridin-2-yl)-ethanone To a −60° C. solution of 2,6-dimethyl pyridine (48 mL, 457 mmol) in tetrahydrofuran (800 mL) was added n-butyl lithium (183 mL, 2.5 M in hexanes, 457 mmol) over 30 minutes. The resulting red solution was stirred at −60° C. for 1 hour, and then treated with a solution of benzo[1,3]dioxole-5-carboxylic acid methoxy-methyl-amide of Step A (415 mmol) in tetrahydrofuran (200 mL) over 1 hour. The resulting reaction mixture was slowly warmed to −20° C. over 3 hours, and then poured over ice (1 kg). The liquid phase was decanted and the ice was washed with methyl tert-butyl ether (1L). The combined organic extracts were washed with saturated aqueous sodium chloride (3×100 mL), dried with magnesium sulfate and concentrated in vacuo to yield the title compound crude (102 g). Recrystallization from toluene yielded the title compound as a yellow solid (57 g, 49% over two steps).

Step C: Preparation of 1-Benzo[1,3]dioxol-5-yl-2-bromo-2-(6-methyl-pyridin-2-yl)-ethanone To a solution of 1-benzo[1,3]dioxol-5-yl-2-(6-methyl-pyridin-2-yl)-ethanone of Step B (2 g, 7.83 mmol) in acetic acid (15 mL) was slowly added a solution of bromine (0.40 mL, 1 equiv) in acetic acid (5 mL). The resulting reaction mixture was stirred at ambient temperature for 1 h, concentrated in vacuo, diluted with diethyl ether (20 mL) and methylene chloride (10 mL). The resulting suspension was stirred at ambient temperature for 16 hours, and then filtered to yield the title compounds as a light beige solid (3.0 g, 92%).

Step D: Preparation of 2-Benzo[1,3]dioxol-5-yl-3-(6-methyl-pyridin-2-yl)-imidazo[1,2-a]pyrimidine To a solution of 1-Benzo[1,3]dioxol-5-yl-2-bromo-2-(6-methyl-pyridin-2-yl)-ethanone of Step C (50 mg, 0.12 mmol) in dimethylformamide (1.0 mL) was added 2-aminopyrimidine (15 mg, 1.3 equiv), and sodium hydrogen carbonate (30 mg, 3 equiv). The resulting solution was shaken at 80° C. for 3 hours, diluted with ethyl acetate (2 mL) and water (3 mL). The organic extract was concentrated in vacuo and silica gel chromatography (3:1 hexane/acetone) yielded the title compound (14 mg, 35%). HPLC $t_R$=1.75 min, LCMS 331.2 (M+1).

EXAMPLE 2

2-Benzo[1,3]dioxol-5-yl-3-(6-methyl-pyridin-2-yl)-1H-imidazo[1,2-a]imidazole

The title compound was prepared according to procedures analogous to those described in Example 1. HPLC $t_R$=1.7 min, LCMS 319.2 (M+1).

EXAMPLE 3

2-Benzo[1,3]dioxol-5-yl-6-chloro-3-(6-methyl-pyridin-2-yl-imidazo[1,2-b]pyridazine The title compound was prepared according to procedures analogous to those described in Example 1. HPLC $t_R$=2.12 min, LCMS 365.2 (M+1).

EXAMPLE 4

2-Benzo[1,3]dioxol-5-yl-3-(6-methyl-pyridin-2-yl)-imidazo[1,2-a]pyridine

The title compound was prepared according to procedures analogous to those described in Example 1. HPLC $t_R$=1.31 min, LCMS 330.2 (M+1).

EXAMPLE 5

Preparation of 6-[2-(6-Methyl-pyridin-2-yl)-imidazo[1,2-a]pyrimidin-3-yl]-quinoline Step A: Preparation of 1-(6-Methyl-pyridin-2-yl)-ethanol
To a −60° C. solution of 6-methyl-pyridine-2-carbaldehyde (25 g, 206 mmol) in tetrahydrofuran (200 mL) was added methyl magnesium bromide (200 mL, 1.4 M in tetrahydrofuran/toluene, 1.36 equiv) over 40 minutes. The reaction mixture was slowly warmed to −10° C. over 90 minutes, and then slowly quenched with saturated aqueous ammonium chloride (75 mL). The liquid phase was decanted from the solids and concentrated in vacuo. The resulting residue was dissolved in methylene chloride, dried over magnesium sulfate, and concentrated in vacuo to yield the title compound (28 g, 100%).

Step B: Preparation of 1-(6-Methyl-pyridin-2-yl)-ethanone
To a −75° C. solution of oxalyl chloride (20 mL, 225 mmol, 1.1 equiv) in methylene chloride (300 mL) was slowly added a solution of dimethylsulfoxide (32 mL, 2.2 equiv) in methylene chloride (400 mL) over 1 hour. The resulting solution was stirred at −75° C. for 10 min, and then slowly treated with a solution of 1-(6-methyl-pyridin-2-yl)-ethanol of Step A (28 g, 204 mmol, 1 equiv) in methylene chloride (600 mL). The reaction mixture was stirred for 10 min at the same temperature, and then slowly treated with triethylamine (140 mL, 1.02 mol, 5 equiv). The resulting mixture was warmed to 20° over 2 hours, and then quenched with water (500 mL). The organic phase was separated, dried over magnesium sulfate and concentrated in vacuo to yield the crude material. Silica gel chromatography (3:1 hexanes/ethyl acetate) yielded the title compound (25.36 g, 92%).

Step C: Preparation of 1-(6-Methyl-pyridin-2-yl)-2-quinolin-6-yl-ethanone
To a solution of 6-chloro-quinoline (2.08 g, 12.3 mmol) in tetrahydrofuran (50 mL) was added 1-(6-methyl-pyridin-2-yl)-ethanone of Step B (2.0 g, 14.8 mmol, 1.1 equiv), palladium acetate (0.055 g, 0.25 mmol, 0.02 equiv), 2-dicyclohexylphosphino-2'-(N,N-dimethylamino)biphenyl (0.197 g, 0.50 mmol, 0.04 equiv), and potassium tert-butoxide (3.76 g, 30.75 mmol, 2.2 equiv). The resulting reaction mixture was heated to 80° C. for 18 hours, then cooled down to 20° C., and slowly treated with acetic acid (3 mL). The resulting solids were filtered off, and the mother liquor was concentrated in vacuo. Silica gel chromatography (3:1 hexane/acetone) yielded the title compound (2.52 g, 78%).

Step D: Preparation of 2-Bromo-1-(6-methyl-pyridin-2-yl)-2-quinolin-6-yl-ethanone
To a stirred solution of 1-(6-methyl-pyridin-2-yl)-2-quinolin-6-yl-ethanone of Step C (1.13 g, 4.3 mmol) in acetic acid (40 mL) was slowly added a solution of bromine (0.22 ml, 4.3 mmol, 1 equiv) in acetic acid (5 mL) over 2 minutes. After stirring at the ambient temperature for 3 hours the reaction mixture was concentrated in vacuo, and the residue was triturated with a mixture of ethyl acetate (20 mL) and ether (20 mL). The crude hydrobromide was converted to the free base by treating with saturated aqueous sodium hydrogen carbonate. The product was extracted with ethyl acetate, the combined organics were washed with saturated aqueous sodium chloride and concentrated in vacuo. Silica gel chromatography (9:1 methylene chloride/acetonitrile) provided title compound as a yellow oil (0.95 g).

Step E: Preparation of 6-[2-(6-Methyl-pyridin-2-yl)-imidazo[1,2-a]pyridin-3-yl]-quinoline
A solution of 2-bromo-1-(6-methyl-pyridin-2-yl)-2-quinolin-6-yl-ethanone of Step D (60 mg, 0.176 mmol) in dimethylformamide (1 mL) was treated with 2-aminopyridine (50 mg, 0.53 mmol, 3 equiv), and heated to 80° C. over 4.5 hours. After cooling down, the mixture was treated with water and extracted with ethyl acetate. The organics were concentrated in vacuo and reverse phase column chromatography (a gradient from 5-30% acetonitrile in 0.1% aqueous formic acid) provided the title compound (14.7 mg, 25%). HPLC $t_R$=1.71 min, LCMS 337.3 (M+1).

EXAMPLE 6

6-[2-(6-Methyl-pyridin-2-yl)-imidazo[1,2-a]pyrazin-3-yl]-quinoline

The title compound was prepared according to procedures analogous to those described in Example 5. HPLC $t_R$=2.0 min, LCMS 338.4 (M+1).

EXAMPLE 7

6-[3-(6-Methyl-pyridin-2-yl)-imidazo[1,2-a]pyridin-2-yl]-quinoline

The title compound was prepared according to procedures analogous to those described in Example 5. HPLC $t_R$=1.30 min, LCMS 337.4 (M+1).

EXAMPLE 8

6-[3-(6-Methyl-pyridin-2-yl)-imidazo[1,2-a]pyrimidin-2-yl]-quinoline

The title compound was prepared according to procedures analogous to those described in Example 5. HPLC $t_R$=1.28 min, LCMS 338.2 (M+1).

EXAMPLE 9

6-[6-(6-Methyl-pyridin-2-yl)-imidazo[2,1-b][1,3,4]thiadiazol-5-yl]-quinoline

The title compound was prepared according to procedures analogous to those described in Example 5. HPLC $t_R$=1.90 min, LCMS 344.3 (M+1).

EXAMPLE 10

6-[6-(6-Methyl-pyridin-2-yl)-imidazo[2,1-b]thiazol-5-yl]-quinoline

The title compound was prepared according to procedures analogous to those described in Example 5. HPLC $t_R$=1.70 min, LCMS 343.3 (M+1).

EXAMPLE 11

6-[8-Methyl-2-(6-methyl-pyridin-2-yl)-imidazo[1,2-a]pyridin-3-yl]-quinoline

The title compound was prepared according to procedures analogous to those described in Example 5. HPLC $t_R$=1.85 min, LCMS 351.3 (M+1).

EXAMPLE 12

6-[7-Methyl-2-(6-methyl-pyridin-2-yl)-imidazo[1,2-a]pyridin-3-yl]-quinoline

The title compound was prepared according to procedures analogous to those described in Example 5. HPLC $t_R$=2.10 min, LCMS 351.3 (M+1).

EXAMPLE 13

6-[6-Methyl-2-(6-methyl-pyridin-2-yl)-imidazo[1,2-a]pyridin-3-yl]-quinoline

The title compound was prepared according to procedures analogous to those described in Example 5. HPLC $t_R$=1.96 min, LCMS 351.3 (M+1).

EXAMPLE 14

6-[3-(6-Methyl-pyridin-2-yl)-7H-imidazo[1,2-a]imidazol-2-yl]-quinoline

The title compound was prepared according to procedures analogous to those described in Example 5. HPLC $t_R$=2.11 min, LCMS 326.3 (M+1).

EXAMPLE 15

1-Methyl-6-[3-(6-methyl-pyridin-2-yl)-imidazo[1,2-a]pyrimidin-2-yl]-1H-benzotriazole The title compound was prepared according to procedures analogous to those described in Example 5. HPLC $t_R$=2.60 min, LCMS 342.3 (M+1).

EXAMPLE 16

1-Methyl-6-[2-(6-methyl-pyridin-2-yl)-imidazo[112-a]pyridin-3-yl]-1H-benzotriazole The title compound was prepared according to procedures analogous to those described in Example 5. HPLC $t_R$=1.90 min, LCMS 341.3 (M+I).

EXAMPLE 17

6-[3-Methyl-6-(6-methyl-pyridin-2-yl)-imidazo[2,1-b]thiazol-5-yl]-quinoline

The title compound was prepared according to procedures analogous to those described in Example 5. HPLC $t_R$=2.10 min, LCMS 357.3 (M+1).

EXAMPLE 18

6-[2-Methyl-6-(6-methyl-pyridin-2-yl)-imidazo[2,1-b]thiazol-5-yl]-quinoline

The title compound was prepared according to procedures analogous to those described in Example 5. HPLC $t_R$=1.90 min, LCMS 357.3 (M+1).

EXAMPLE 19

6-[7-Methyl-2-(6-methyl-pyridin-2-yl)-imidazo[1,2-a]pyrimidin-3-yl]-quinoline The title compound was prepared according to procedures analogous to those described in Example 5. HPLC $t_R$=1.80 min, LCMS 352.4 (M+1).

EXAMPLE 20

2-(6-Methyl-pyridin-2-yl)-3-quinolin-6-yl-imidazo[12-a]pyrimidin-7-ylamine

The title compound was prepared according to procedures analogous to those described in Example 5. HPLC $t_R$=1.90 min, LCMS 353.4 (M+1).

EXAMPLE 21

6-[7-Methyl-2-(6-methyl-pyridin-2-yl)-6-nitro-imidazo[1,2-a]pyridin-3-yl]-quinoline The title compound was prepared according to procedures analogous to those described in Example 5. HPLC $t_R$=2.90 min, LCMS 396.3 (M+1).

EXAMPLE 22

1-Methyl-6-[2-(6-methyl-pyridin-2-yl)-imidazo[12-a]pyrimidin-3-yl]-1H-benzotriazole The title compound was prepared according to procedures analogous to those described in Example 5. HPLC $t_R$=1.60 min, LCMS 342.4 (M+I).

EXAMPLE 23

1-Methyl-6-[6-(6-methyl-pyridin-2-yl)-imidazo[2,1-b]thiazol-5-yl]-1H-benzotriazole The title compound was prepared according to procedures analogous to those described in Example 5. HPLC $t_R$=1.80 min, LCMS 347.3 (M+1).

EXAMPLE 24

1-Methyl-6-[6-(6-methyl-pyridin-2-yl)-imidazo[2,1-b][1,3,4]thiadiazol-5-yl]-1H-benzotriazole The title compound was prepared according to procedures analogous to those described in Example 5. HPLC $t_R$=1.90 min, LCMS 348.3 (M+1).

EXAMPLE 25

2-Methyl-5-[2-(6-methyl-pyridin-2-yl)-imidazo[1,2-a]pyrimidin-3-yl]-2H-benzotriazole The title compound was prepared according to procedures analogous to those described in Example 5. HPLC $t_R$=1.90 min, LCMS 342.3 (M+1).

EXAMPLE 26

3-(2-Methyl-2H-benzotriazol-5-yl)-2-(6-methyl-pyridin-2-yl)-imidazo[1,2-a]pyrimidin-7-ylamine The title compound was prepared according to procedures analogous to those described in Example 5. HPLC $t_R$=2.0 min, LCMS 357.4 (M+1).

EXAMPLE 27

2-Methyl-5-[6-(6-methyl-pyridin-2-yl)-imidazo[2,1-b]thiazol-5-yl]-2H-benzotriazole The title compound was prepared according to procedures analogous to those described in Example 5. HPLC $t_R$=2.0 min, LCMS 347.3 (M+1).

EXAMPLE 28

2-Methyl-5-[6-(6-methyl-pyridin-2-yl)-imidazo[2,1-b][1,3,4]thiadiazol-5-yl]-2H-benzotriazole The title compound was prepared according to procedures analogous to those described in Example 5. HPLC $t_R$=1.74 min, LCMS 348.3 (M+1).

EXAMPLE 29

2-(6-Methyl-pyridin-2-yl)-3-quinolin-6-yl-imidazo[1,2-a]pyrimidin-7-ol

The title compound was prepared according to procedures analogous to those described in Example 5. HPLC $t_R$=1.31 min, LCMS 354.4 (M+1).

EXAMPLE 30

1-Methyl-6-[6-(6-methyl-pyridin-2-yl)-2-methylsulfanyl-imidazo[2,1-b][1,3,4]thiadiazol-5-yl]-1H-benzotriazole The title compound was prepared according to procedures analogous to those described in Example 5. HPLC $t_R$=2.26 min, LCMS 394.3 (M+1).

EXAMPLE 31

Dimethyl-[2-(6-methyl-pyridin-2-yl)-3-quinolin-6-yl-imidazo[1,2-a]pyrimidin-7-yl]-amine The title compound was prepared according to procedures analogous to those described in Example 5. HPLC $t_R$=2.30 min, LCMS 381.4 (M+1).

EXAMPLE 32

2-Methyl-5-[3-methyl-6-(6-methyl-pyridin-2-yl)-imidazo[2,1-b]thiazol-5-yl]-2H-benzotriazole The title compound was prepared according to procedures analogous to those described in Example 5. HPLC $t_R$=1.88 min, LCMS 361.4 (M+1).

EXAMPLE 33

2-Methyl-5-[2-methyl-6-(6-methyl-pyridin-2-yl)-imidazo[2,1-b]thiazol-5-yl]-2H-benzotriazole The title compound was prepared according to procedures analogous to those described in Example 5. HPLC $t_R$=2.12 min, LCMS 361.4 (M+1).

EXAMPLE 34

2-(6-Methyl-pyridin-2-yl)-3-pyridin-4-yl-imidazo[1,2-a]pyridine

The title compound was prepared according to procedures analogous to those described in Example 5. HPLC $t_R$=1.26 min, LCMS 287.4 (M+1).

EXAMPLE 35

2-(6-Methyl-pyridin-2-yl)-3-pyridin-4-yl-imidazo[1,2-a]pyrimidine

The title compound was prepared according to procedures analogous to those described in Example 5. HPLC $t_R$=1.17 min, LCMS 288.4 (M+1).

EXAMPLE 36

2-(6-Methyl-pyridin-2-yl)-3-pyridin-4-yl-imidazo[1,2-a]pyrimidin-7-ylamine

The title compound was prepared according to procedures analogous to those described in Example 5. HPLC $t_R$=1.20 min, LCMS 303.3 (M+1).

EXAMPLE 37

3-Benzothiazol-6-yl-2-(6-methyl-pyridin-2-yl)-imidazo[1,2-a]pyrimidin-7-ylamine

The title compound was prepared according to procedures analogous to those described in Example 5. HPLC $t_R$=1.80 min, LCMS 359.4 (M+1).

EXAMPLE 38

1-Methyl-6-[6-(6-cyclopropyl-pyridin-2-yl)-imidazo[2,1-b][1,3,4]thiadiazol-5-yl]-1H-benzotriazole Step A: Preparation of 2-Bromo-6-formylpyridine To a stirred solution of 2.5 M n-butyllithium in hexane (8.6 mL, 21.5 mmol) under $N_2$, cooled to −78° C., was added dropwise a solution of 2,6-dibromopyridine (5.10 g, 21.5 mmol) in dry THF (30 mL) at such a rate that the internal temperature was below −70° C. After complete addition, the reaction mixture was stirred at −78° C. for 15 min, and then treated with anhydrous DMF (2.6 mL, 33.3 mmol). After 15 min, the reaction mixture was treated successively with acetic acid (1.36 mL) and water (21.5 mL) and then warmed to RT. The reaction mixture was poured into ethyl acetate (75 mL). The phases were separated. The aqueous phase was extracted with ethyl acetate (25 mL). The combined organic phases were washed with brine (35 mL), dried ($MgSO_4$), filtered and concentrated to afford 3.33 g (18.0 mmol, 84%) of the desired product as a white solid.

Step B: Preparation of 2-Bromo-6-(1,3-dioxolan-2-yl)pyridine

A mixture of 2-bromo-6-formylpyridine of Step A (839.1 mg, 4.5 mmol), ethylene glycol (1.2 mL, 22.69 mmol) and a catalytic amount of p-toluene sulfonic acid in toluene (21 mL) was heated at reflux using a Dean Stark trap for 2.5 h. The cooled reaction mixture was concentrated. The resulting residue was dissolved in $CH_2Cl_2$, adsorbed onto silica gel and purified on a Biotage 40 M column with SIM using 10-20% ethyl acetate in hexane as the eluent to afford 919.1 mg (4.01 mmol, 89%) of the desired acetal.

Step C: Preparation of 2-Cyclopropyl-6-(1,3-dioxolan-2-yl)pyridine (WO2003087304)

To a stirred solution of 0.5 M zinc chloride in THF (9.1 mL, 4.55 mmol) under $N_2$, cooled to −78° C. was added dropwise a solution of 0.5 M cyclopropylmagnesium bromide in THF (9.1 mL, 4.55 mmol). The reaction mixture was warmed to RT and stirred for 1 h. The resulting zincate was transferred via syringe to a sealed tube containing a solution of 2-bromo-6-(1,3-dioxolan-2-yl)pyridine of Step B (694.3 mg, 3.03 mmol) and Pd(PPh$_3$)$_4$ in dry THF (3 mL). The reaction mixture was degassed, sealed and heated at 120° C. for 2 h. The reaction mixture was cooled to RT and partitioned between ethyl acetate (100 mL) and saturated aqueous $NH_4Cl$ (50 mL). The phases were separated. The aqueous phase was extracted with ethyl acetate (15 mL). The combined organic phases were dried ($MgSO_4$), filtered and concentrated. The resulting residue was dissolved in $CH_2Cl_2$, adsorbed onto silica gel and purified on a Biotage 40S column with SIM using 10% ethyl acetate in hexane as the eluent to afford 538.2 mg (2.82 mmol, 93%) of the desired product as a bright yellow liquid.

Step D: Preparation of 6-cyclopropyl-2-pyridinecarboxaldehyde

A mixture of 2-cyclopropyl-6-(1,3-dioxolan-2-yl)pyridine of Step C (538.2 mg, 2.82 mmol) in 10% aqueous HCl (5 mL) and THF (10 mL) was heated at reflux for 18 h. The cooled reaction mixture was cooled to 0° C. and quenched with saturated aqueous $NaHCO_3$. The reaction mixture was poured into $CHCl_3$ (20 mL). The phases were separated. The aqueous phase was extracted with $CHCl_3$ (10 mL). The combined organic phases were dried ($MgSO_4$), filtered and concentrated. The resulting residue was purified on a Biotage 40S column using 10% ethyl acetate in hexane as the eluent to afford 351.0 mg (2.38 mmol, 85%) of the desired aldehyde as a clear oil.

Step E: Preparation of 1-Methyl-6-[6-(6-cyclopropyl-pyridin-2-yl)-imidazo[2,1-b][1,3,4]thiadiazol-5-yl]-1H-benzotriazole The title compound was prepared according to procedures analogous to those described in Example 5. HPLC $t_R$=1.90 min, LCMS 374.3 (M+1).

EXAMPLE 39

6-[2-(6-Methyl-pyridin-2-yl)-imidazo[1,2-a]pyrimidin-3-yl]-quinoxaline

The title compound is prepared according to procedures analogous to those described in Example 5.

EXAMPLE 40

2-(6-Methyl-pyridin-2-yl)-3-quinoxalin-6-yl-imidazo[1,2-a]pyrimidin-7-ylamine

The title compound is prepared according to procedures analogous to those described in Example 5.

EXAMPLE 41

6-[6-(6-Methyl-pyridin-2-yl)-imidazo[2,1-b]thiazol-5-yl]-quinoxaline

The title compound is prepared according to procedures analogous to those described in Example 5.

EXAMPLE 42

6-[6-(6-Methyl-pyridin-2-yl)-imidazo[2,1-b][1,3,4]thiadiazol-5-yl]-quinoxaline

The title compound is prepared according to procedures analogous to those described in Example 5.

EXAMPLE 43

6-[2-(6-Methyl-pyridin-2-yl)-imidazo[112-a]pyridin-3-yl]-quinoxaline

The title compound is prepared according to procedures analogous to those described in Example 5.

EXAMPLE 44

2-[2-(6-Methyl-pyridin-2-yl)-imidazo[1,2-a]pyrimidin-3-yl]-[1,5]naphthyridine

The title compound is prepared according to procedures analogous to those described in Example 5.

EXAMPLE 45

2-(6-Methyl-pyridin-2-yl)-3-[1,5]naphthyridin-2-yl-imidazo[1,2-a]pyrimidin-7-ylamine The title compound is prepared according to procedures analogous to those described in Example 5.

EXAMPLE 46

2-[6-(6-Methyl-pyridin-2-yl)-imidazo[2,1-b]thiazol-5-yl]-[1,5]naphthyridine

The title compound is prepared according to procedures analogous to those described in Example 5.

EXAMPLE 47

2-[6-(6-Methyl-pyridin-2-yl)-imidazo[2,1-b][1,3,4]thiadiazol-5-yl]-[1,5]naphthyridine The title compound is prepared according to procedures analogous to those described in Example 5.

EXAMPLE 48

2-[2-(6-Methyl-pyridin-2-yl)-imidazo[1,2-a]pyridin-3-yl]-[1,5]naphthyridine

The title compound is prepared according to procedures analogous to those described in Example 5.

EXAMPLE 49

3-(2,3-Dimethyl-3H-benzoimidazol-5-yl)-2-(6-methyl-pyridin-2-yl)-imidazo[1,2-a]pyrimidine The title compound is prepared according to procedures analogous to those described in Example 5.

EXAMPLE 50

3-(2,3-Dimethyl-3a,7a-dihydro-3H-benzoimidazol-5-yl)-2-(6-methyl-pyridin-2-1-imidazo[1,2-a]pyrimidin-7-ylamine The title compound is prepared according to procedures analogous to those described in Example 5.

EXAMPLE 51

1,2-Dimethyl-6-[6-(6-methyl-pyridin-2-yl)-imidazo[2,1-b]thiazol-5-yl]-3a,7a-dihydro-1H-benzoimidazole The title compound is prepared according to procedures analogous to those described in Example 5.

EXAMPLE 52

1,2-Dimethyl-6-[6-(6-methyl-pyridin-2-yl)-imidazo[2,1-b][1,3,4]thiadiazol-5-yl]-3a,7a-dihydro-1H-benzoimidazole The title compound is prepared according to procedures analogous to those described in Example 5.

EXAMPLE 53

1,2-Dimethyl-6-[2-(6-methyl-pyridin-2-yl)-imidazo[1,2-a]pyridin-3-yl]-1H-benzoimidazole The title compound is prepared according to procedures analogous to those described in Example 5.

EXAMPLE 54

3-(2-Methyl-benzooxazol-6-yl)-2-(6-methyl-pyridin-2-yl)-imidazo[1,2-a]pyrimidine The title compound is prepared according to procedures analogous to those described in Example S.

EXAMPLE 55

3-(2-Methyl-3a,7a-dihydro-benzooxazol-6-yl)-2-(6-methyl-pyridin-2-yl)-imidazo[12-a]pyrimidin-7-ylamine The title compound is prepared according to procedures analogous to those described in Example 5.

EXAMPLE 56

2-Methyl-6-[6-(6-methyl-pyridin-2-yl)-imidazo[21-b]thiazol-5-yl]-3a,7a-dihydro-benzooxazole The title compound is prepared according to procedures analogous to those described in Example 5.

EXAMPLE 57

2-Methyl-6-[6-(6-methyl-pyridin-2-yl)-imidazo[2,1-b][1,3,4]thiadiazol-5-yl]-3a,7a-dihydro-benzooxazole The title compound is prepared according to procedures analogous to those described in Example 5.

EXAMPLE 58

2-Methyl-6-[2-(6-methyl-pyridin-2-yl)-imidazo[1,2-a]pyridin-3-yl]-benzooxazole

The title compound is prepared according to procedures analogous to those described in Example 5.

EXAMPLE 59

6-[2-(6-Methyl-pyridin-2-yl)-imidazo[1,2-a]pyrimidin-3-yl]-quinazoline

The title compound is prepared according to procedures analogous to those described in Example 5.

EXAMPLE 60

2-(6-Methyl-pyridin-2-yl)-3-quinazolin-6-yl-imidazo[1,2-a]pyrimidin-7-ylamine

The title compound is prepared according to procedures analogous to those described in Example 5.

EXAMPLE 61

6-[6-(6-Methyl-pyridin-2-yl)-imidazo[2,1-b]thiazol-5-yl]-quinazoline

The title compound is prepared according to procedures analogous to those described in Example 5.

EXAMPLE 62

6-[6-(6-Methyl-pyridin-2-yl)-imidazo[2,1-b][1,3,4]thiadiazol-5-yl]-quinazoline

The title compound is prepared according to procedures analogous to those described in Example 5.

EXAMPLE 63

6-[2-(6-Methyl-pyridin-2-yl)-imidazo[12-a]pyridin-3-yl]-quinazoline

The title compound is prepared according to procedures analogous to those described in Example 5.

EXAMPLE 64

3-Methyl-5-[6-(6-methyl-pyridin-2-yl)-imidazo[2,1-b]thiazol-5-yl]-3H-[1,2,3]triazolo[4,5-b]pyridine Step A: Preparation of 6,N2-dimethyl-pyridine-2,3-diamine
2-Chloro-6-methyl-3-nitropyridine (2.5 g, 14.5 mmol) was stirred in 1.0 M solution of methylamine (40 ml, 40 mmol) in methanol at 70° C. for 60 min. After cooling to ambient temperature, and methanol (60 ml) and 10% palladium on activated carbon were added and the resulting mixture was shaken under 40 psi of hydrogen gas at ambient temperature for 30 min. The mixture was filtered through a pad of Celite and concentrated in vacuum. Chromatography on silica gel, eluting with a mixture dichloromethane-methanol-38% aqueous ammonia (9:1:0.1) yielded the title compound (1.65 g, 83%).

Step B: Preparation of 3,5-dimethyl-3H-[1,2,3]triazolo[4,5-b]pyridine
6,N2-dimethyl-pyridine-2,3-diamine of Step A (1.5 g, 10.9 mmol), 2-methyl-2-nitrosooxy-propane (1.6 ml, 13.1 mmol), acetic acid (2.6 ml, 43.6 mmol), and ethanol (50 ml) were stirred at 60° C. for 60 min. After cooling to ambient temperature, sodium hydrogen carbonate (3 g) was added and the resulting mixture was stirred at ambient temperature for 20 min. The mixture was diluted with dichloromethane (20 ml), solids were filtered off, and the obtained solution was concentrated in vacuum. Chromatography on silica gel, eluting with dichloromethane-acetonitrile (93:7) yielded the title compound (1.23 g, 76%).

Step C: Preparation of 1-(6-methyl-pyridin-2-yl)-2-(3-methyl-3H-[1,2,3]triazolo[4,5-b]pyridin-5-yl)-ethanone
To a stirred solution of 3,5-dimethyl-3H-[1,2,3]triazolo[4,5-b]pyridine of Step B (200 mg, 1.35 mmol), 6-methylpyridine-2-carboxylic acid methoxy-methyl-amide (268 mg, 1.49 mmol), and tetrahydrofuran (5 ml) a 1.0 M solution of lithium hexamethyldisilazide (3.0 ml, 3.0 mmol) was added –78° C. in 10 min. The mixture was warmed up to ambient temperature in 90 min and stirred at the same temperature for 3 h. Methanol (10 ml) and 10% hydrochloric acid (1.5 ml) were added and stirring continued for 18 h. Sodium hydrogen carbonate (5 g) and dichloromethane (10 ml) were added and stirring continued for 10 min. After filtering off solids, the obtained mixture was concentrated. Chromatography on silica gel, eluting with ethyl acetate-hexane (2:3) yielded the title compound (110 mg, 30%).

Step D: Preparation of 2-bromo-1-(6-methyl-pyridin-2-yl)-2-(3-methyl-3H-1,2,3]triazolo[4,5-b]pyridin-5-yl)-ethanone hydrobromide.

To a stirred solution of 1-(6-methyl-pyridin-2-yl)-2-(3-methyl-3H-[1,2,3]triazolo[4,5-b]pyridin-5-yl)-ethanone of Step C (110 mg, 0.41 mmol) in acetic acid (3 ml) a solution of bromine (0.021 ml, 0.41 mmol) in acetic acid (2 ml) was added at ambient temperature in 5 min and the resulting mixture was stirred at the same temperature for 3 h. Ether (15 ml) was added and stirring was continued for 1 h. The liquid was decanted and the obtained yellow solid was dried in vacuum to yield the title compound (130 mg, 74%).

Step E: Preparation of 3-methyl-5-[6-(6-methyl-pyridin-2-yl)-imidazo[2,1-b]thiazol-5-yl]-3H-[1,2,3]triazolo[4,5-b]pyridine
A mixture of 2-bromo-1-(6-methyl-pyridin-2-yl)-2-(3-methyl-3H-1,2,3]triazolo[4,5-b]pyridin-5-yl)-ethanone hydrobromide of Step D (30 mg, 0.07 mmol), thiazol-2-ylamine (30 mg, 0.3 mmol), and ethanol (1.5 ml) was stirred at 80° C. for 90 min. After cooling to ambient temperature, the mixture was concentrated to dryness. Chromatography on a reverse phase column, eluting with 5 to 30% gradient of acetonitrile in 0.1% aqueous formic acid yielded the title compound (5.9 mg, 24%). HPLC $t_R$=2.0 min, LCMS 348.3 (M+1).

EXAMPLE 65

3-Methyl-5-[6-(6-methyl-pyridin-2-yl)-imidazo[2,1-b][13.4]thiadiazol-5-yl]-3H-[1,2,3]triazolo[4,5-b]pyridine The title compound was prepared according to procedures analogous to those described in Example 64. HPLC $t_R$=1.6 min, LCMS 349.3 (M+1).

EXAMPLE 66

2-Methyl-5-[2-(6-methyl-pyridin-2-yl)-7H-imidazo[1,2-a]imidazol-3-yl]-2H-benzotriazole The title compound was prepared according to procedures analogous to those described in Example 64. HPLC $t_R$=1.8 min, LCMS 330.3 (M+1).

All publications, including but not limited to, issued patents, patent applications, and journal articles, cited in this application are each herein incorporated by reference in their entirety.

Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:
1. A compound of the formula (Ia) or (Ib):

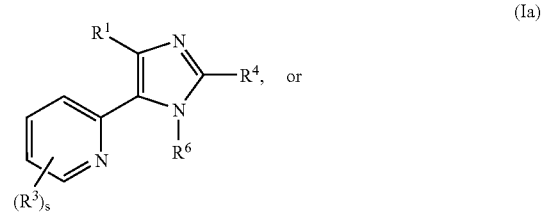

(Ib)

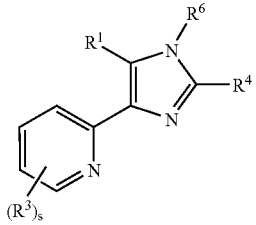

or a pharmaceutically acceptable salt or tautomer thereof wherein:

R$^1$ is an optionally substituted saturated, unsaturated, or aromatic C$_3$-C$_{20}$ mono-, bi- or polycyclic ring optionally containing at least one heteroatom selected from the group consisting of N, O and S;

each R$^3$ is independently selected from the group consisting of: hydrogen, halo, halo(C$_1$-C$_6$)alkyl, (C$_1$-C$_6$)alkyl, (C$_2$-C$_6$)alkenyl, (C$_2$-C$_6$)alkynyl, perhalo(C$_1$-C$_6$)alkyl, (C$_5$-C$_{10}$)heteroaryl, (C$_5$-C$_{10}$)heterocycle, (C$_3$-C$_{10}$)cycloalkyl, hydroxy, (C$_1$-C$_6$)alkoxy, perhalo(C$_1$-C$_6$) alkoxy, phenoxy, (C$_5$-C$_{10}$)heteroaryl-O—, (C$_5$-C$_{10}$)heterocycle-O—, (C$_3$-C$_{10}$)cycloalkyl-O—, (C$_1$-C$_6$)alkyl-S—, (C$_1$-C$_6$)alkyl-SO$_2$—, (C$_1$-C$_6$)alkyl-NH—SO$_2$—, nitro, cyano, amino, Ph(CH$_2$)$_{1-6}$NH—, (C$_1$-C$_6$)alkylamino, [(C$_1$-C$_6$)alkyl]$_2$-amino, (C$_1$-C$_6$)alkyl-SO$_2$—NH—, amino(C═O)—, aminoSO$_2$—, (C$_1$-C$_6$)alkyl-(C═O)—NH—, (C$_1$-C$_6$)alkyl-(C═O)—[((C$_1$-C$_6$)alkyl)-N]—, phenyl-(C═O)—NH—, phenyl-(C═O)—[((C$_1$-C$_6$)alkyl)-N]—, (C$_1$-C$_6$)alkyl-(C═O)—, phenyl-(C═O)—, (C$_5$-C$_{10}$)heteroaryl-(C═O)—, (C$_5$-C$_{10}$)heterocycle-(C═O)—, (C$_3$-C$_{10}$)cycloalkyl-(C═O)—, HO—(C═O)—, (C$_1$-C$_6$)alkyl-O—(C═O)—, H$_2$N(C═O)—(C$_1$-C$_6$)alkyl-NH—(C═O)—, [(C$_1$-C$_6$)alkyl]$_2$-N—(C═O)—, phenyl-NH—(C═O)—, phenyl-[((C$_1$-C$_6$)alkyl)-N]—(C═O)—, (C$_5$-C$_{10}$)heteroaryl-NH—(C═O)—, (C$_5$-C$_{10}$)heterocycle-NH—(C═O)—, (C$_3$-C$_{10}$)cycloalkyl-NH—(C═O)— and (C$_1$-C$_6$)alkyl-(C═O)—O—, where R$^3$ is optionally substituted by at least one substituent independently selected from (C$_1$-C$_6$)alkyl, (C$_1$-C$_6$)alkoxy, halo(C$_1$-C$_6$)alkyl, halo, H$_2$N—, Ph(CH$_2$)$_{1-6}$NH—, and (C$_1$-C$_6$)alkylNH—;

s is an integer from one to four; and

R$^4$ and R$^6$ taken together with the atoms to which they are attached form a core fused heteroaromatic.

2. A compound of claim 1, wherein R$^3$ is a (C$_1$-C$_6$)alkyl or a (C$_3$-C$_{10}$)cycloalkyl group.

3. A compound of claim 2, wherein R$^3$ is a methyl or a cyclopropyl group.

4. A compound of clams 1, wherein R$^1$ is

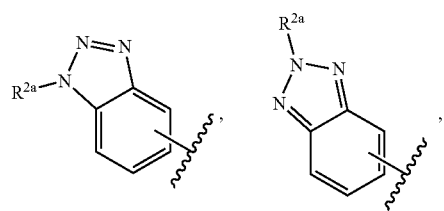

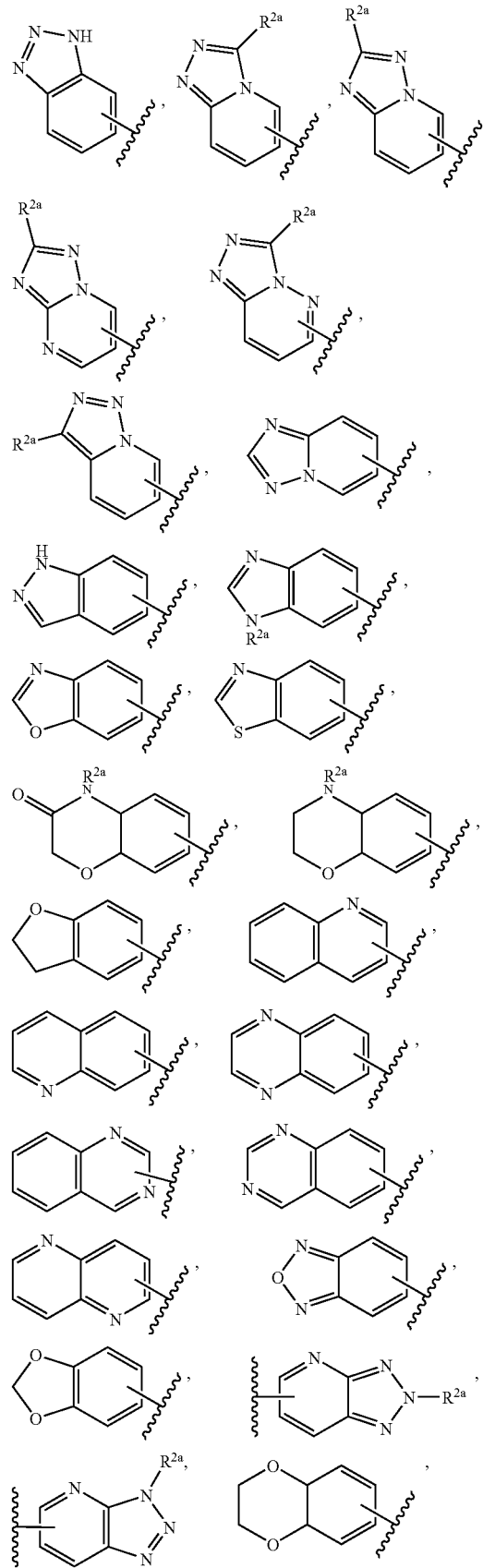

-continued

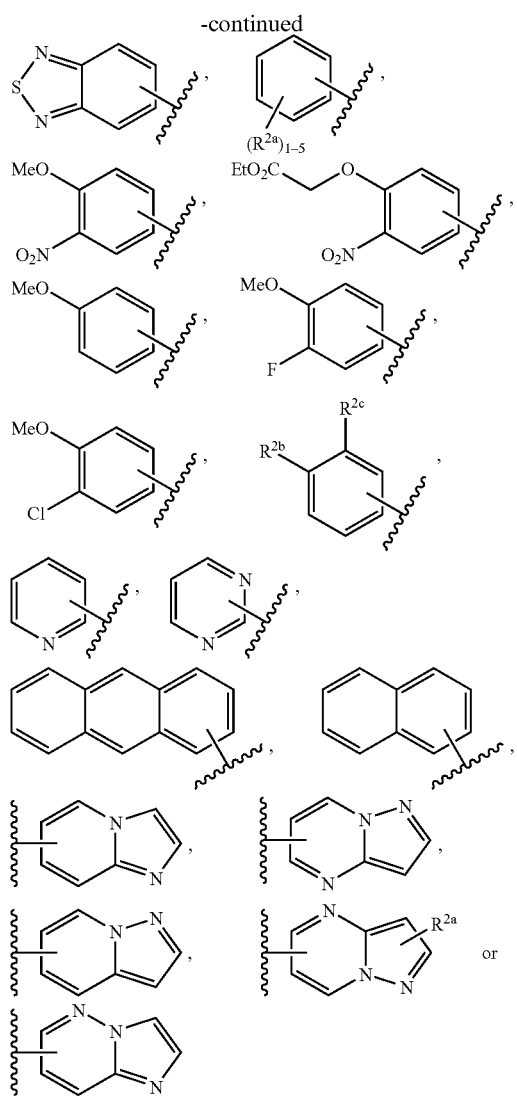

wherein $R^{2a}$ is independently selected from the group consisting of: hydrogen, $(C_1-C_6)$alkyl, $(C_2-C_6)$alkenyl, $(C_2-C_6)$alkynyl, $(C_3-C_{10})$cycloalkyl, $(C_5-C_{10})$aryl, $(C_1-C_6)$alkyl$(C_5-C_{10})$aryl, amino, carbonyl, carboxyl, $(C_5-C_{10})$heteroaryl, $(C_5-C_{10})$heterocyclyl, $(C_1-C_6)$alkoxy, nitro, halo, and hydroxyl; and where alkyl, alkenyl, alkynyl, cycloalkyl, aryl, amino, heteroaryl, heterocyclyl, and alkoxy of $R^{2a}$ is optionally substituted by at least one moiety independently selected from the group consisting of hydrogen, halo, $(C_1-C_6)$alkyl, $(C_2-C_6)$alkenyl, $(C_2-C_6)$alkynyl, perhalo$(C_1-C_6)$alkyl, phenyl, $(C_3-C_{10})$cycloalkyl, $(C_5-C_{10})$heteroaryl, $(C_1-C_{10})$heterocycle, formyl, —CN, $(C_1-C_6)$alkyl-(C=O)—, phenyl-(C=O)—, HO—(C=O)—, $(C_1-C_6)$alkyl-O—(C=O)—, $(C_1-C_6)$alkyl-NH—(C=O)—, $((C_1-C_6)$alkyl$)_2$-N—(C=O)—, phenyl-NH—(C=O)—, phenyl-$[((C_1-C_6)$alkyl$)$-N]—(C=O)—, nitro, amino, $(C_1-C_6)$alkylamino, $((C_1-C_6)$alkyl$)_2$-amino, $(C_1-C_6)$alkyl-(C=O)—NH—, $(C_1-C_6)$alkyl-(C=O)-$[((C_1-C_6)$alkyl$)$-N]—, phenyl-(C=O)—NH—, phenyl-(C=O)—$[((C_1-C_6)$alkyl$)$-N]—, $H_2N$—(C=O)—NH—, $(C_1-C_6)$alkyl-NH—(C=O)—NH—, $((C_1-C_6))$alkyl$)_2N$—(C=O)—NH—, $(C_1-C_6)$alkyl-HN—(C=O)—$[((C_1-C_6)$alkyl$)$-N]—, $((C_1-C_6)$alkyl$)_2N$—(C=O)—$[(C_1-C_6)$alkyl-N]—, phenyl-NH—(C=O)—NH—, (phenyl$)_2N$—(C=O)—NH—, phenyl-HN—(C=O)—$[((C_1-C_6)$alkyl$)$-N]—, (phenyl-$)_2N$—(C=O)—$[((C_1-C_6)$alkyl$)$-N]—, $(C_1-C_6)$alkyl-O—(C=O)—NH—, $(C_1-C_6)$alkyl-O—(C=O)—$[((C_1-C_6)$alkyl$)$-N]—, phenyl-O—(C=O)—NH—, phenyl-O—(C=O)—$[((C_1-C_6)$alkyl$)$-N]—, $(C_1-C_6)$alkyl-$SO_2NH$—, phenyl-$SO_2NH$—, $(C_1-C_6)$alkyl-$SO_2$—, phenyl-$SO_2$—, hydroxy, $(C_1-C_6)$alkoxy, perhalo$(C_1-C_6)$alkoxy, phenoxy, $(C_1-C_6)$alkyl-(C=O)—O—, phenyl-(C=O)—O—, $H_2N$—(C=O)—O—, $(C_1-C_6)$alkyl-HN—(C=O)—O—, $((C_1-C_6)$alkyl$)_2N$—(C=O)—O—, phenyl-HN—(C=O)—O—, and (phenyl$)_2N$—(C=O)—O—; and $R^{2b}$ and $R^{2c}$ taken together with the atoms to which they are attached form an optionally substituted mono-, bi- or polycyclic, saturated, unsaturated, or aromatic ring system optionally containing at least one heteroatom selected from the group consisting of N, O and S.

5. A compound selected from the group consisting of:
6-[2-(6-Methyl-pyridin-2-yl)-imidazo[1,2-a]pyrimidin-3-yl]-quinoline;
2-Benzo[1,3]dioxol-5-yl-3-(6-methyl-pyridin-2-yl)-imidazo[1,2-a]pyrimidine;
6-[3-(6-Methyl-pyridin-2-yl)-imidazo[1,2-a]pyrimidin-2-yl]-quinoline;
1-Methyl-6-[3-(6-methyl-pyridin-2-yl)-imidazo[1,2-a]pyrimidin-2-yl]-1H-benzotriazole;
6-[7-Methyl-2-(6-methyl-pyridin-2-yl)-imidazo[1,2-a]pyrimidin-3-yl]-quinoline;
2-(6-Methyl-pyridin-2-yl)-3-quinolin-6-yl-imidazo[1,2-a]pyrimidin-7-ylamine;
1-Methyl-6-[2-(6-methyl-pyridin-2-yl)-imidazo[1,2-a]pyrimidin-3-yl]-1H-benzotriazole;
2-Methyl-5-[2-(6-methyl-pyridin-2-yl)-imidazo[1,2-a]pyrimidin-3-yl]-2H-benzotriazole;
3-(2-Methyl-2H-benzotriazole-5-yl)-2-(6-methyl-pyridin-2-yl)-imidazo[1,2-a]pyrimidin-7-ylamine;
2-6-Methyl-pyridin-2-yl)-3-quinolin-6-yl-imidazo[1,2-a]pyrimidin-7-yl;
Dimethyl-[2-(6-methyl-pyridin-2-yl)-3-quinolin-6-yl-imidazo[1,2-a]pyrimidin-7-yl]amine;
2-(6-Methyl-pyridin-2-yl)-3-pyridin-4-yl-imidazo[1,2-a]pyrimidine;
2-(6-Methyl-pyridin-2-yl)-3-pyridin-4-yl-imidazo[1,2-a]pyrimidine-7-ylamine; and
3-Benzotriazole-6-yl-2-(6-methyl-pyridin-2-yl)-imidazo[1,2-a]pyrimidin-7-ylamine.

6. A pharmaceutical composition comprising a compound of claim 1 and a pharmaceutically acceptable carrier.

* * * * *

UNITED STATES PATENT AND TRADEMARK OFFICE
CERTIFICATE OF CORRECTION

PATENT NO. : 7,417,041 B2 Page 1 of 1
APPLICATION NO. : 10/783251
DATED : August 26, 2008
INVENTOR(S) : Blumberg et al.

It is certified that error appears in the above-identified patent and that said Letters Patent is hereby corrected as shown below:

Column 57, lines 50-51, should read
"R4 and R6 taken together with the atoms to which they are attached form a pyrimidyl moiety."

Signed and Sealed this

Twenty-second Day of June, 2010

David J. Kappos
*Director of the United States Patent and Trademark Office*